United States Patent
Penn, IV et al.

(10) Patent No.: US 10,736,625 B1
(45) Date of Patent: Aug. 11, 2020

(54) SYSTEM AND METHOD FOR SUTURING BIOLOGICAL MATERIAL

(71) Applicant: ACUSTITCH, LLC, Orlando, FL (US)

(72) Inventors: John N. Penn, IV, Orlando, FL (US); John M. Menezes, Las Vegas, NV (US)

(73) Assignee: ACUSTITCH, LLC, Orlando, FL (US)

( * ) Notice: Subject to any disclaimer, the term of this patent is extended or adjusted under 35 U.S.C. 154(b) by 0 days.

(21) Appl. No.: 16/662,635

(22) Filed: Oct. 24, 2019

(51) Int. Cl.
*A61B 17/04* (2006.01)
*A61B 17/062* (2006.01)
*A61B 17/06* (2006.01)

(52) U.S. Cl.
CPC ...... *A61B 17/0491* (2013.01); *A61B 17/0469* (2013.01); *A61B 17/0625* (2013.01); *A61B 17/0482* (2013.01); *A61B 17/06066* (2013.01)

(58) Field of Classification Search
CPC ............ A61B 17/0491; A61B 17/0469; A61B 17/0625; A61B 17/0482; A61B 17/06066; A61B 17/0483; A61B 17/04; A61B 17/06114; A61B 17/062; A61B 2017/2927; A61B 2017/0608; A61B 2017/2929
See application file for complete search history.

(56) References Cited

U.S. PATENT DOCUMENTS

| | | |
|---|---|---|
| 1,620,550 A | 3/1927 | Howe |
| 4,133,339 A | 1/1979 | Naslund |
| 4,345,601 A | 8/1982 | Fukuda |
| 4,406,237 A | 9/1983 | Eguchi et al. |
| 4,527,564 A | 7/1985 | Eguchi et al. |
| 4,799,483 A | 1/1989 | Kraff |
| 4,799,484 A | 1/1989 | Smith et al. |
| 4,899,746 A | 2/1990 | Brunk |
| 5,002,564 A | 3/1991 | McGregor et al. |
| 5,258,013 A | 11/1993 | Granger et al. |
| 5,458,616 A | 10/1995 | Granger et al. |
| 5,562,686 A | 10/1996 | Sauer et al. |
| 5,693,072 A | 12/1997 | McIntosh |
| 5,935,138 A | 8/1999 | McJames, II et al. |
| 8,273,103 B2 | 9/2012 | Waeschle |
| 8,617,207 B1 | 12/2013 | Henderson |

(Continued)

FOREIGN PATENT DOCUMENTS

| | | |
|---|---|---|
| WO | 201322959 | 2/2013 |
| WO | 2013022959 | 2/2013 |

(Continued)

OTHER PUBLICATIONS

Concept Laser a GE Additive Company, https://www.concept-laser.de/en/home.html, 2016.

(Continued)

*Primary Examiner* — George J Ulsh
(74) *Attorney, Agent, or Firm* — Terry M. Sanks, Esq.; Beusse Sanks, PLLC

(57) ABSTRACT

A suturing system including at least one drive gear with a plurality of outward protrusions and a needle with a first end, a second end, and a plurality of indentations therebetween wherein the plurality of indentations engage with the plurality of outward protrusions of the drive gear to circularly rotate the needle. Additional suturing systems and a method of suturing biological material are also included.

23 Claims, 21 Drawing Sheets

(56) References Cited

U.S. PATENT DOCUMENTS

| | | |
|---|---|---|
| 8,663,249 B2 | 3/2014 | Badhwar |
| 8,721,664 B2 | 5/2014 | Ruff et al. |
| 8,932,308 B2 | 1/2015 | Ibrahim et al. |
| 9,192,376 B2 | 11/2015 | Almodovar |
| 9,724,087 B2 | 8/2017 | Berry |
| 9,724,089 B1 | 8/2017 | Martin et al. |
| 9,962,155 B2 | 5/2018 | Meade et al. |
| 9,986,997 B2 | 6/2018 | Meade et al. |
| 2006/0069396 A1* | 3/2006 | Meade ............... A61B 17/0482 606/144 |
| 2006/0224184 A1 | 10/2006 | Stefanchik et al. |
| 2008/0132919 A1* | 6/2008 | Chui ................. A61B 17/0482 606/145 |
| 2009/0209980 A1 | 8/2009 | Harris |
| 2009/0209982 A1 | 8/2009 | Hoerstrup et al. |
| 2015/0127024 A1 | 5/2015 | Berry |
| 2018/0116659 A1 | 5/2018 | Walters et al. |

FOREIGN PATENT DOCUMENTS

| | | |
|---|---|---|
| WO | 2013158622 | 10/2013 |
| WO | 2018132081 | 7/2018 |

OTHER PUBLICATIONS

EndoEvolution, Endo360, The Technology, http://www.endoevolution.com/endo360/technology, 2018.

ErgoSuture Corp, http://www.ergosuture.com/our-services-1.html, 2008.

Johnson & Johnson, Medical Devices Companies, https://www.ethicon.com/na/products/wound-closure/automated-suture-device/proxisure-suturing-device, 2019.

International Search Report, dated Mar. 30, 2020.

* cited by examiner

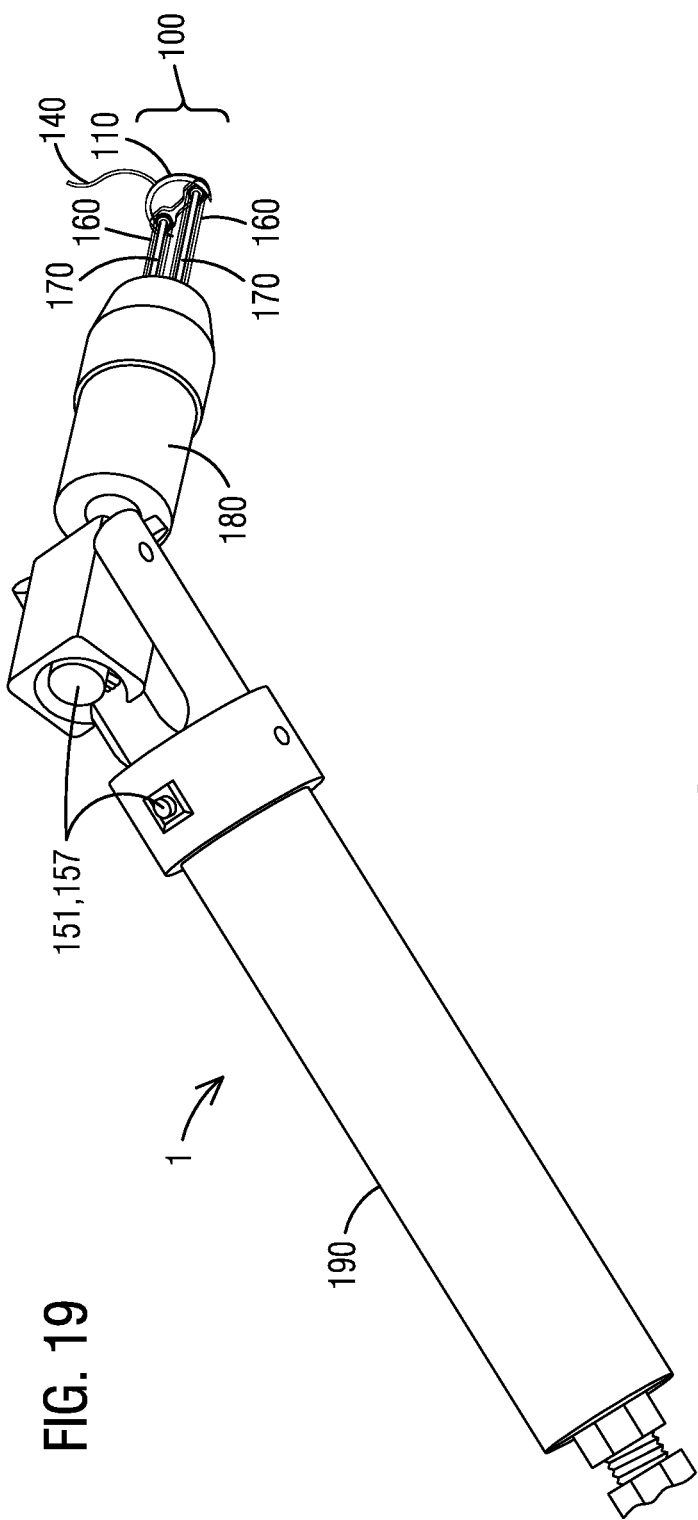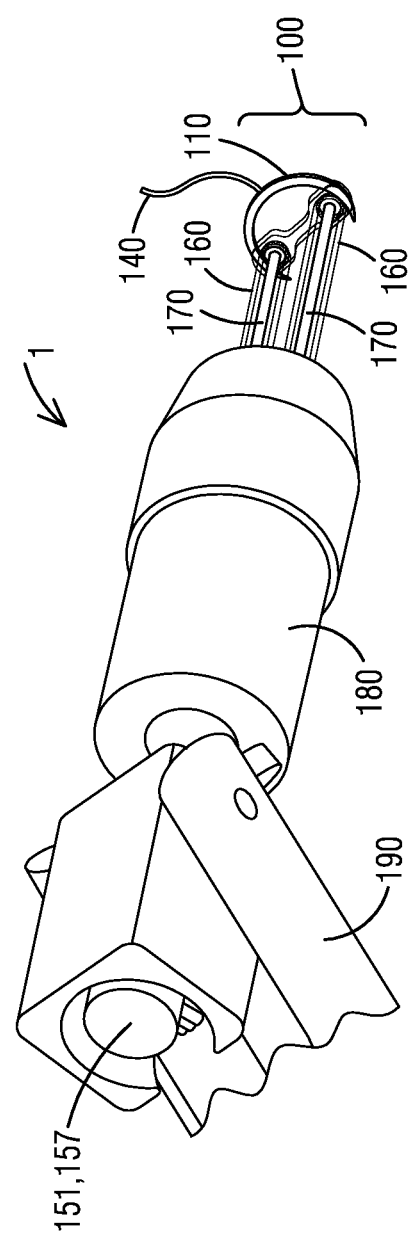

SYSTEM AND METHOD FOR SUTURING BIOLOGICAL MATERIAL

BACKGROUND

Embodiments relate to medical devices for surgical wound repair and, in particular, of suturing devices for automatic or semi-automatic application of sutures.

Currently the repair of long wounds is performed by the hand of a trained medical professional, often a surgeon. For both surgically or traumatically created full thickness wounds of the skin and subcutaneous tissues this involves the layered repair of the subcutaneous portion (fat, superficial fascia, and deep dermis) of the wound as one layer and the upper dermis and epidermis as a second layer. This is typically performed with single interrupted buried resorbable sutures followed by either a continuous running subcuticular resorbable (more superficial dermal) suture, a through-and-through interrupted suture nonabsorbable suture, or a continuous running suture similar to a baseball stitch which is also dermal and epidermal.

This process can be quite time consuming when treating long wounds, similar to those required in plastic surgery and body lifts. In practice, for each stitch or throw, a needle driver is typically required. During this process the suturing professional clamps the needle distally, towards the non-pointed end, with the needle driver, then drives or pushes the pointed end through the medium following its natural curved path until the needle point emerges. Finally, the professional unclamps the needle, and re-clamps it proximally, towards the pointed end, pulling it the rest of the way through the material or flesh. The technique requires one hand with a forcep to control the tissue and the second hand to control the needle driver, each motion adding time to the procedure, even with an assistant retracting tissue or cutting suture for the primary surgeon. In trauma or veterinarian applications the complexities of applying sutures to a wound in general and long wounds in particular are exacerbated by the usual absence of a controlled surgical environment. Longer operating times are associated with higher complication rates from both the anesthetic as well as higher risks of wound infection. Therefore, a mechanism which can improve the efficiency of motion and reduce operative times can improve outcomes.

Inventions found in the prior art have tried to mitigate this issue by automating the suturing process. However, they have found limited success. Particularly, disclosures in the prior art have focused on using curved needles that are actuated by friction. This solution is bulky and often presents performance problems when the movement of the needle through the medium is impeded by higher densities and thicknesses. In those situations, the lack of friction between the needle and the driving wheels causes the needle to get stuck. Additionally, these technologies inherently lack precise needle control because of traction loss between the driving wheels and the smooth metal needle.

Other approaches have focused on operating the needle with a pushing system based on a pawl that engages the needle. However, these systems can only rotate the needle in one direction and in predetermined steps before the pawl must be reset to reengage the needle. In addition, these systems are all hand operated devices that constantly require user input and cannot operate automatically.

Therefore, in emergency, in-the-field trauma, and planned surgeries, both in human and veterinarian applications, the benefits of semi-automatic and automatic operation of a suturing device that can provide controlled angular rotation of the needle accrue resulting in a simpler, more accurate and more efficient process for the medical professional translating to better, faster and safer patient care.

SUMMARY

Accordingly, the inventors have developed a suturing system and method for automated or semi-automated operation by controlling the angular rotation of a suturing needle in a plurality of directions. The suturing system may include at least one drive gear with a plurality of outward protrusions and a needle with a first end, a second end, and a plurality of indentations therebetween wherein the plurality of indentations engage with the plurality of outward protrusions of the drive gear to circularly rotate the needle.

Another suturing system may include a handle, a drive mechanism mounted to the handle, a support body having a proximate end and a distal end, the proximate end connected to the handle, a head rotatably mounted on the distal end of the support body whereby the head rotates perpendicular to the support body, and a pivot drive mechanism connected to the head on one end and to a pivot drive mechanism on the other, wherein the pivot drive mechanism causes the head to rotate. The suturing system may further include at least one drive gear with a plurality of radially mounted outward protrusions and a through axle with opposing ends, each opposing end having an engaged portion, the at least one drive gear mounted to the head, at least one driveshaft with a driven end and an engaging end, the driven end connected to the drive mechanism, and the engaging end in mating contact with the engaged portion of the at least one gear; and a needle with a first end, a second end, and a plurality of indentations therebetween, wherein the plurality of indentations engages with the plurality of outward protrusions of the drive gear to rotate the needle in a circular manner.

Another suturing system may include a handle, a drive mechanism and a pivot drive mechanism mounted to the handle, a support body having a proximate end and a distal end, the proximate end connected to the pivot drive mechanism, a head mounted on the distal end of the support body whereby the head rotates with the support body when the pivot drive mechanism is actuated. The suturing system may further include at least one drive gear with a plurality of radially mounted outward protrusions mounted to the head, at least one driveshaft connecting the drive mechanism and the at least one gear; and a needle with a first end, a second end, and a plurality of indentations therebetween, wherein the plurality of indentations engage with the plurality of outward protrusions of the drive gear to rotate the needle in a circular manner.

The method comprises perforating the biological material with at least one of a first end and a second end of the needle, the needle further comprising an arcuate body, the arcuate body including a proximate end connected to the first end and a distal end connected to the second end, the suturing system further comprising a suture attached to the needle. The method further comprises rotating the needle in at least one of a clockwise and a counterclockwise direction for at least one rotation to pull the suture through the biological material by engaging a plurality of indentations between the first end and the second end of the needle with a plurality of outward protrusions of at least one drive gear of the head, wherein the at least one drive gear is connected to the drive mechanism. The method also comprises rotating the head at least one of clockwise or counterclockwise with the pivot drive mechanism; perforating the biological material with at least one of the first end and the second end and rotating the needle in at least one of a clockwise and a counterclockwise direction for at least one rotation to pull the suture through the biological material by engaging a plurality of indentations between the first end and the second end of the needle with a plurality of outward protrusions of the at least one drive gear of the head, wherein the at least one drive gear is connected to the drive mechanism.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered limiting of its scope, the embodiments will be described and explained with additional specificity and detail through the use of the accompanying drawings in which:

FIG. 19 is a perspective view of a suturing system according to an embodiment disclosed herein;

FIG. 20 is a detailed view of the head of the suturing system of FIG. 19, according to an embodiment disclosed herein;

DETAILED DESCRIPTION

Figure 1:
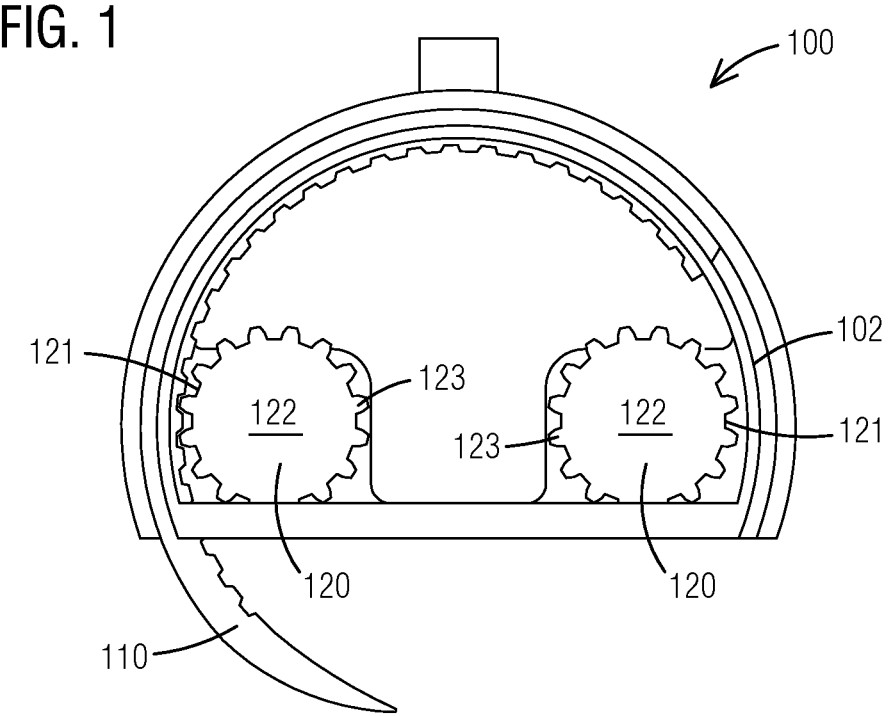
FIG. 1 is a front view of a head of a suturing system according to an embodiment disclosed herein.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

As used herein, the term "biological material" means any part of a human or animal capable of being sutured including but not limited to skin, muscle, tendons, etc. The term "biological material" may also be used to denote any organic or inorganic material capable of being stitched.

Figure 2:
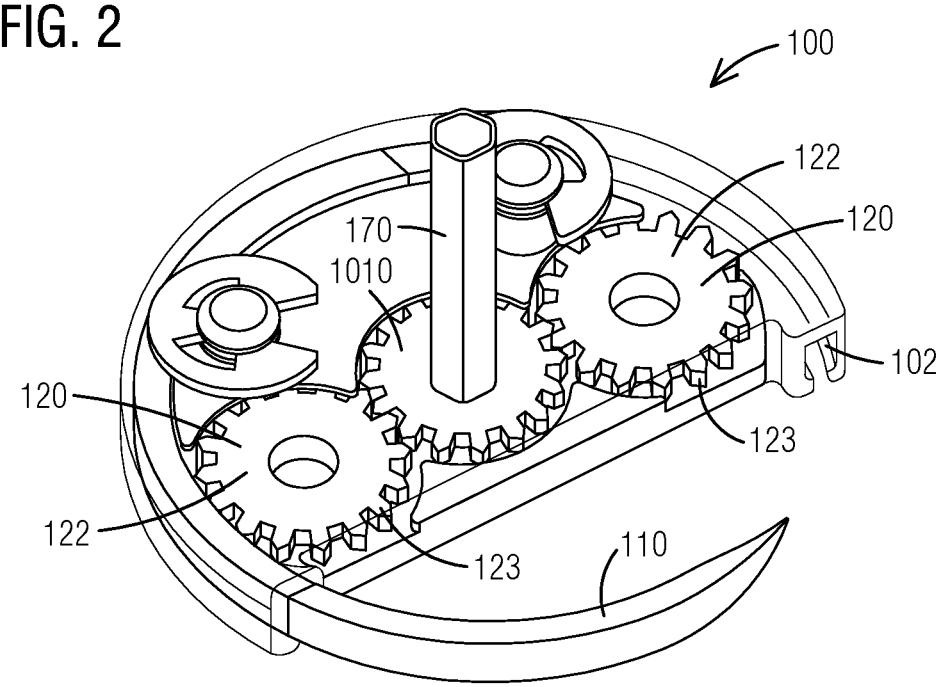
FIG. 2 is a perspective view of a head of a suturing system according to an embodiment disclosed herein.
Figure 3A:
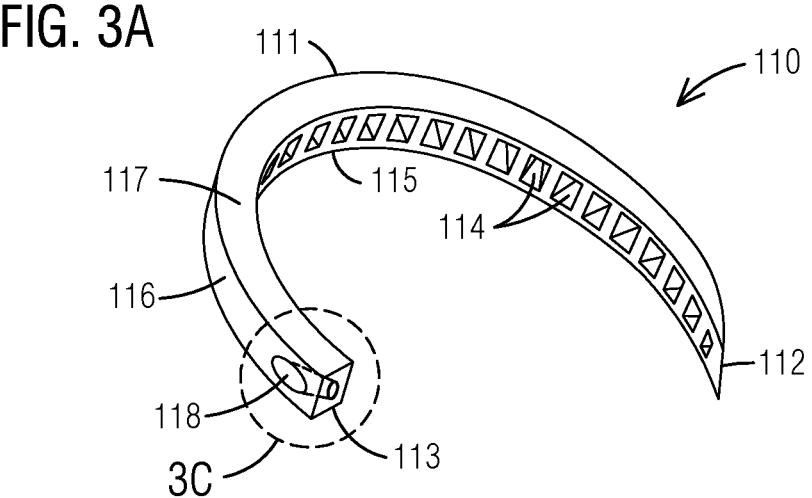
FIG. 3A is a perspective view of a needle having an arcuate body according to an embodiment disclosed herein.
Figure 3B:
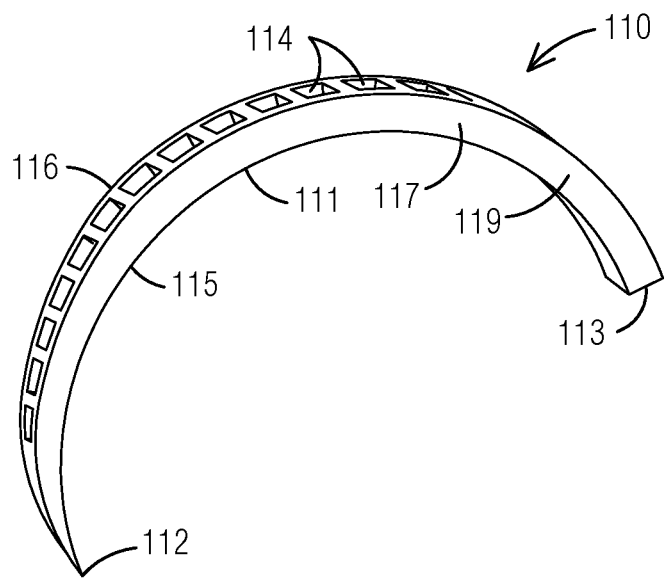
FIG. 3B is another perspective view of the needle of FIG. 3A according to an embodiment disclosed herein.
Figure 3C:
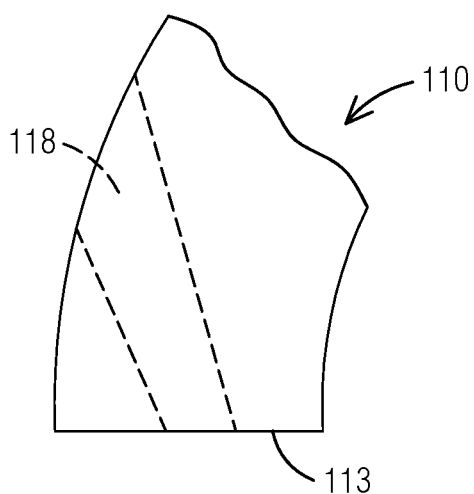
FIG. 3C is detailed view of an end of the needle of FIGS. 3A-3B according to an embodiment disclosed herein.
Figure 4A:
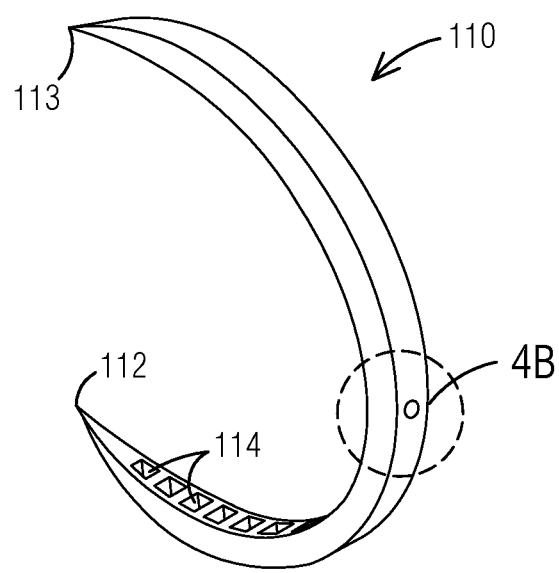
FIG. 4A is a perspective view of a needle having an arcuate body according to an embodiment disclosed herein.
Figure 4B:
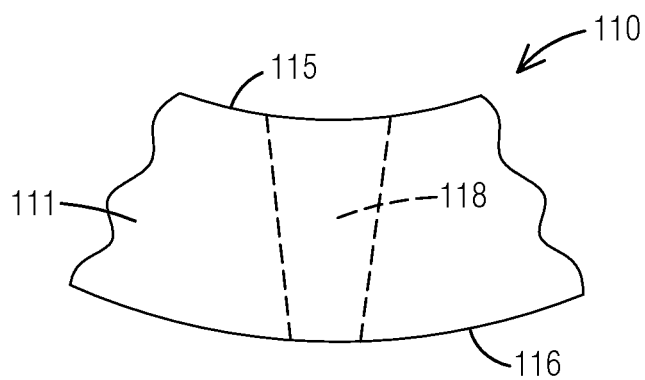
FIG. 4B is detailed view of an end of the needle of FIG. 4A according to an embodiment disclosed herein.
Figure 5:
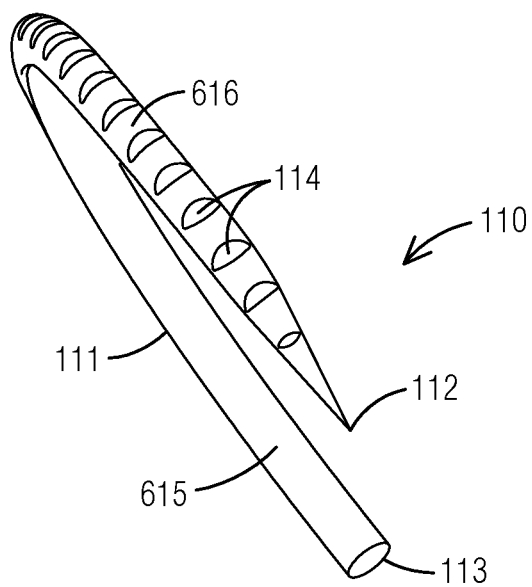
FIG. 5 is a perspective view of a needle having an arcuate body according to an embodiment disclosed herein.
Figure 6:
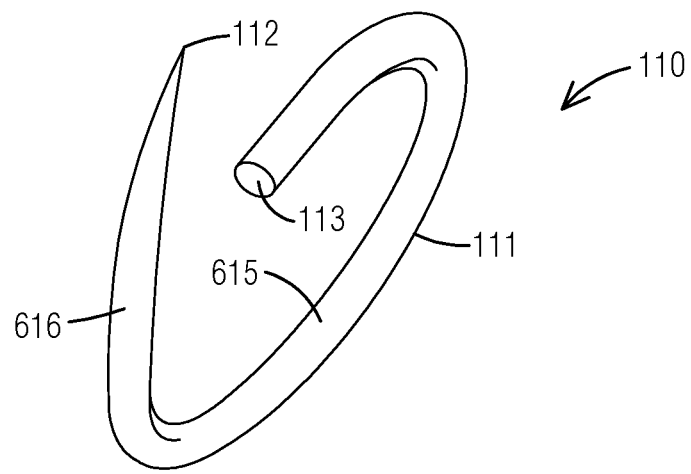
FIG. 6 is a perspective view of a needle having a toroidal helix body according to an embodiment disclosed herein.

Referring now to FIG. 1 and FIG. 2, a front view and a perspective view, respectively, of an embodiment of a suturing system 1 with a head 100, according to an aspect of the present disclosure, is shown. The head 100 may comprise a needle 110 and at least one drive gear 120. As a non-limiting example, the embodiment of the head 100 shown in FIG. 1 has two drive gears 120. The at least one drive gear 120 may include a plurality of outward protrusions 123. In an embodiment, the drive gear 120 may have a round shape wherein each of the outward protrusions 123 may be equally spaced around the circumference 121 of the drive gear 120. In other embodiments the drive gear 120 may be round and the plurality of outward protrusions 123 may be asymmetrically located around the circumference 121 of the drive gear 120. In yet some other embodiments, the drive gear 120 may be oval shaped and the plurality of outward protrusions 123 may be either symmetrically or asymmetrically distributed through the perimeter of the drive gear 120. In other embodiments, the drive gear 120 may have a perimeter (or circumference) 121 and a drive face 122 perpendicular to the perimeter, where the plurality of outward protrusions 123 may be located on either the perimeter, the drive face 122, or both. Still, in some other embodiments, the drive gear 120 may be at least one of a cam, a spur gear, a helical gear, a bevel gear, a worm gears, and a pinion.

FIG. 3 through FIG. 6 are perspective views of non-limiting embodiments of a needle 110 according to an embodiment disclosed herein. The needle 110 may include a body 111, a first end 112, a second end 113, and a plurality of indentations 114. The first end 112 may be connected to a proximate part of the body 111 and the second end 113 may be connected to a distal part of the body 111. As a non-limiting example, the first end 112, the body 111, and the second end 113 may form a single continuous structure with no discernible joints or connection points. In an embodiment, the plurality of indentations 114 may be disposed inside the body 111 between the first end 112 and the second end 113. As a non-limiting example, the plurality of indentations 114 may be a repetitive machine pattern. As used herein, the term "repetitive machine pattern" may include at least two identical intrusions into a material during a manufacturing process. In some non-limiting embodiments, the repetitive machine pattern may be at least one of a series of holes, a series of slots, and knurling. As it may be appreciated by those skilled in the art, the exact configuration of the repetitive machine pattern is non-limiting.

In another embodiment, the body 111 of the needle 110 may have at least one of an arcuate, a cylindrical, a helical, a toroidal, and a toroidal helix shape. In another embodiment, the body 111 may have a cylindrical shape with a constant major diameter that allows for cyclic or repetitive motion. In yet another embodiment, the body 111 may have a cylindrical shape with a constant advancing pitch to enable the cyclic or repetitive motion.

In yet another embodiment, at least one of the first end 112 and the second end 113 of the needle 110 may be a pointed end to penetrate a biological material 3 (further discussed in FIGS. 14A-14E and 18A-18D). As used herein, the term "penetrate" means to insert, pierce, perforate, breach, or stab any organic or inorganic material. In a non-limiting embodiment, at least one the first end 112 and the second end 113 may be at least one of a taper point, a blunt taper point, a cutting-edge point, a reverse cutting-edge point, a taper-cut point, a micro-point spatula curved point, and a blunt end. In another embodiment, at least one of the first end 112 and the second end 113 may comprise cutting edges, such as, but no limited to, four cutting edges terminating in a single point. In other embodiments still, at least one the first end 112 and the second end 113 may comprise a square or four-sided point.

Returning to FIG. 3 through FIG. 4, the body 111 of the needle 110 may include an inner surface 115, an outer surface 116, and at least two side surfaces 117. In a non-limiting embodiment, the inner surface 115, the outer surface 116, and the at least two side surfaces 117 may otherwise be referred to as a contacting surface. As a non-limiting example, the plurality of indentations 114 may be disposed on at least one of the inner surface 115, the outer surface 116, and at least one the side surfaces 117. In those embodiments, the plurality of indentations 114 may pierce at least one of the inner surface 115, the outer surface 116, and at least one the side surfaces 117 into the body 111.

In an embodiment, a suture 140 may be connected to the needle 110 at an attachment point 118. The attachment point 118 may be located in the body 111 between the first end 112 and the second end 113. In some other embodiments, the attachment point 118 may be generally located on at least one of the first end 112 and the second end 113. As an example, in the non-limiting embodiments shown in FIGS. 3A-3C, the attachment point 118 may extend between the outer surface 116 and the second end 113. In other embodiments, the attachment point 118 may be generally located on at least one of the inner surface 115, the outer surface 116, and one of the at least two side surfaces 117. As another example, in the non-limiting embodiment shown in FIG. 4A-4B, the attachment point 118 may be located in the body 111 and may extend between the inner surface 115 and the outer surface 116. In other embodiments, the attachment point 118 may be generally located on at least one of the generally inner surface 615 and the generally outer surface 616.

In some embodiment, the attachment point 118 may be an opening in the body 111. In yet other embodiments, the attachment point 118 may extend between two or more surfaces of the needle 110. In the non-limiting embodiments shown in FIGS. 3A-3C and FIG. 4A-4B, the attachment point 118 is a tapered hole having a larger opening in one surface and a smaller opening in another surface. In other embodiments, the opening may be square or oval shaped. As it may be appreciated by those skilled in the art, the shape and arrangement of the attachment point 118 is non limiting and may be achieved in a plurality of ways.

The suture 140 may be connected to the needle 110 by threading it through the attachment point 118 when the attachment point 118 is an opening in the body 111. In an embodiment, where the attachment point 118 is a tapered opening extending through the body 111, a knot or a bulging part of the suture 140 may be compressed by a narrowing nature of the tapered opening thereby securing the suture 140 to the needle 110. In another embodiment, the attachment point 118 may be a depression in a surface of the needle 110.

In yet another embodiment, the suture 140 may be at least one of glued, bonded, tied, and fused to the body 111. In another embodiment, the suture 140 may be secured to the body 111 at the attachment point 118 during a manufacturing process. In yet another embodiment, the suture 140 may be secured to at least one of the first end 112 and the second end 113. As non-limiting examples, the suture 140 may be at least one of glued, bonded, tied, and fused to at least one of the first end 112 and the second end 113.

Returning to FIG. 5 and FIG. 6, the body 111 of the needle 110 may have a circular cross section further comprising a generally inner surface 615 and a generally outer surface 616. As a non-limiting example, the plurality of indentations 114 may be disposed on at least one of the generally inner surface 615 and the generally outer surface 616. In those embodiments, the plurality of indentations 114 may pierce at least one of at least one of the generally inner surface 615 and the generally outer surface 616 into the body 111.

It may be appreciated by those skilled in the art that the material and method of manufacturing of the needle 110 is non-limiting. As a non-limiting example, the needle 110 may be made from at least one of a metal, a polymer, a ceramic, and a combination thereof. As another non-limiting example, the needle 110 may be manufactured by at least one of milling, machining, casting, layering, injection molding, stamping, gluing, fusing, Metal Injection Molding, Fused Deposition Modeling (FDM), Stereolithography (SLA), Digital Light Processing (DLP), Selective Laser Sintering (SLS), Material Jetting (MJ), Drop on Demand (DOD), Binder Jetting, Direct Metal Laser Sintering (DMLS), Selective Laser Melting (SLM), Electron Beam Melting (EBM), or by any other additive manufacturing process.

It may also be appreciated by those skilled in the art that the material and method of manufacturing of the suture 140 is non-limiting. In some embodiments, the suture 140 may be manufactured out of either a biologically absorbable (resorbable) or non-absorbable material. As a non-limiting example, the suture 140 may be manufactured out of at least one of gut, polydioxanone, poliglecaprone, polyglactin, nylon, polypropylene, silk, and polyester. As another non-limiting example, the suture 140 may be manufactured out of a combination of at least one of gut, polydioxanone, poliglecaprone, polyglactin, nylon, polypropylene, silk, and polyester.

As it may be appreciated by those skilled in the art, at least one of the needle 110 and the suture 140 may be at least one of sterile and disposable. Similarly, in some embodiments the head 100 may be at least one of removable and reusable. At least one of the suturing system 1, the head 100, the needle 110, and the suture 140 may be sterilized using presently known or subsequently developed hospital sterilization methods. In other embodiments, at least one of the suturing system 1, the head 100, the needle 110, and the suture 140 may be sterile and disposable.

Returning to FIG. 1, the plurality of outward protrusions 123 of the at least one drive gear 120 engage with the plurality of indentations 114 of the needle 110 to rotate the needle 110 in a circular fashion. In another embodiment, each of the plurality of outward protrusions 123 may have a plurality of surfaces and each of the plurality of indentations 114 may have a matching plurality of surfaces whereby at least one of the plurality of surfaces of each of the plurality of outward protrusions 123 is in contact with the matching surface of each of the plurality of indentations 114 to effect a better stability of motion as the needle 110 is rotated by the at least one drive gear 120.

Figure 24:
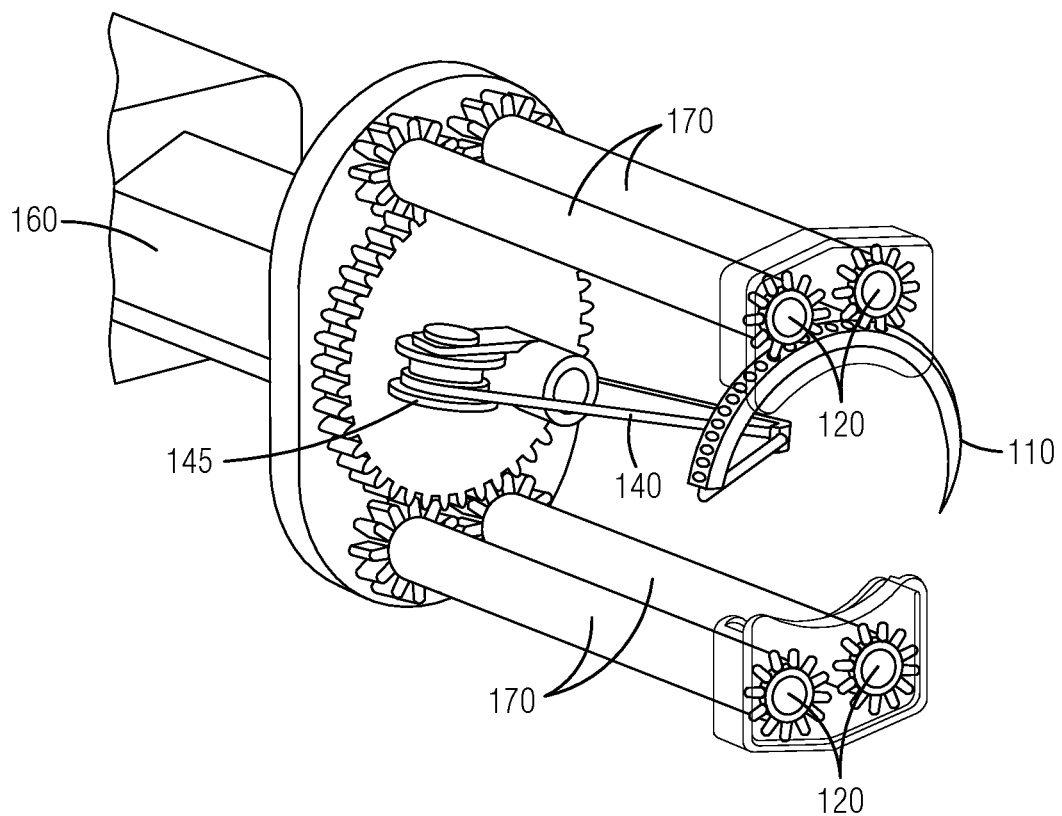
FIG. 24 is a perspective view of a head of a suturing system according to an embodiment disclosed herein.
Figure 25:
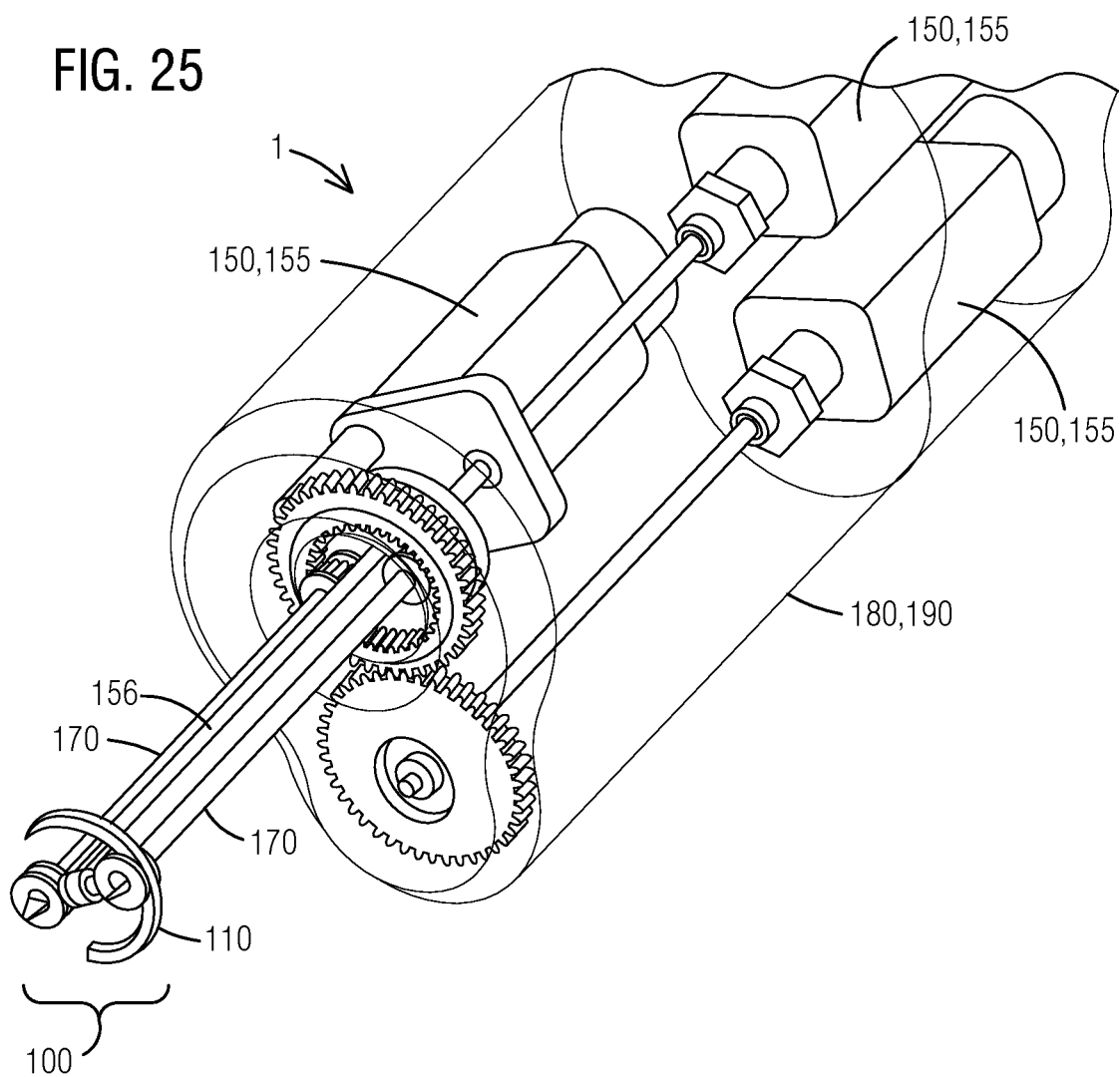
FIG. 25 is a perspective view of a head of a suturing system according to an embodiment disclosed herein.
Figure 26:
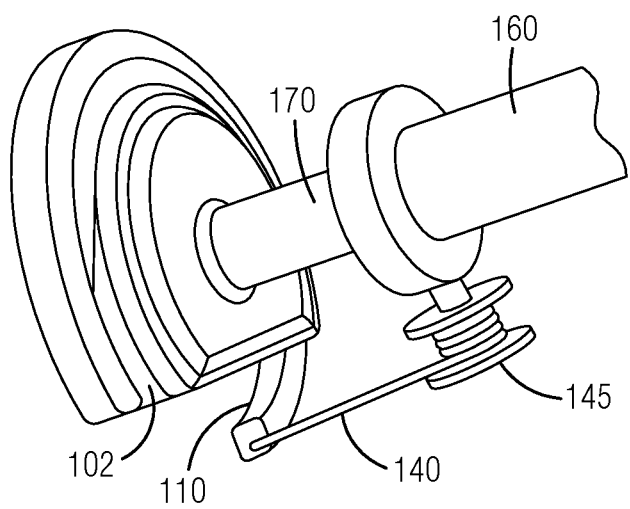
FIG. 26 is a perspective view of a head of a suturing system according to an embodiment disclosed herein.

In an embodiment, the head 100 may include two drive gears 120 configured to rotate synchronously. In those embodiments, the plurality of outward protrusions 123 of at least one of the two drive gears 120 are in engagement with the plurality of indentations 114 of the needle 110 to circularly rotate the needle 110. As a non-limiting example, the embodiments shown in FIGS. 1, 2, 7-9, 10-13, 15-17, 21-23, 25, and 26 include two drive gears 120 to circularly rotate the needle 110. Yet, in the non-limiting example shown in FIG. 24, head 100 includes four drive gears 120.

In some embodiments, the head 100 includes a channel 102 matching the cross-sectional profile of the body 111 of the needle 110 to support the needle 110 as it rotates. In another embodiment, the channel 102 may include at least one guide to engage at least one groove 119. The groove 119 may be located on at least one of the inner surface 115, the outer surface 116, and at least one the side surfaces 117. In yet another embodiment, the groove 119 may be located on at least one of the generally inner surface 615 and the generally outer surface 616.

Figure 7:
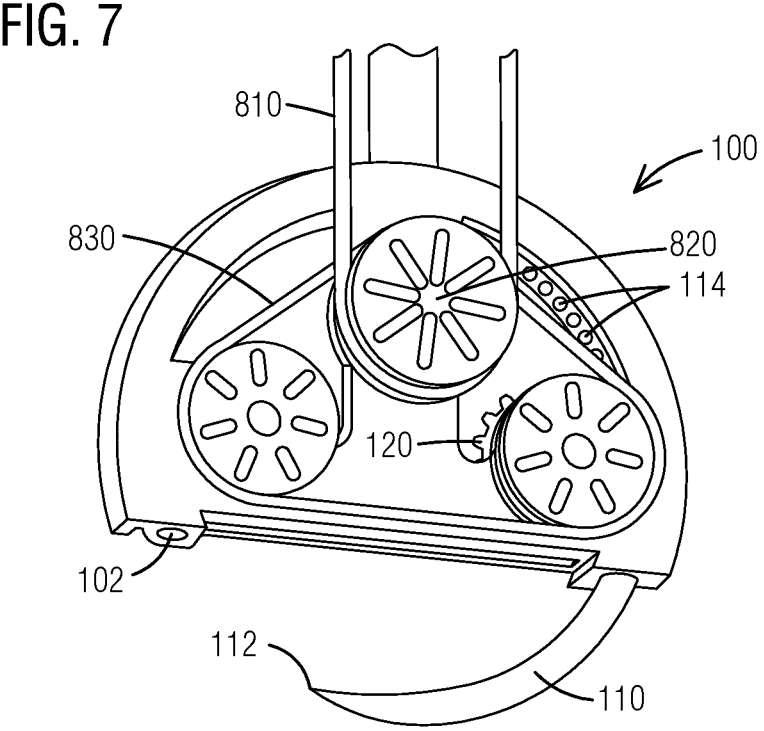
FIG. 7 is a perspective view of a head of a suturing system according to an embodiment disclosed herein.
Figure 8:
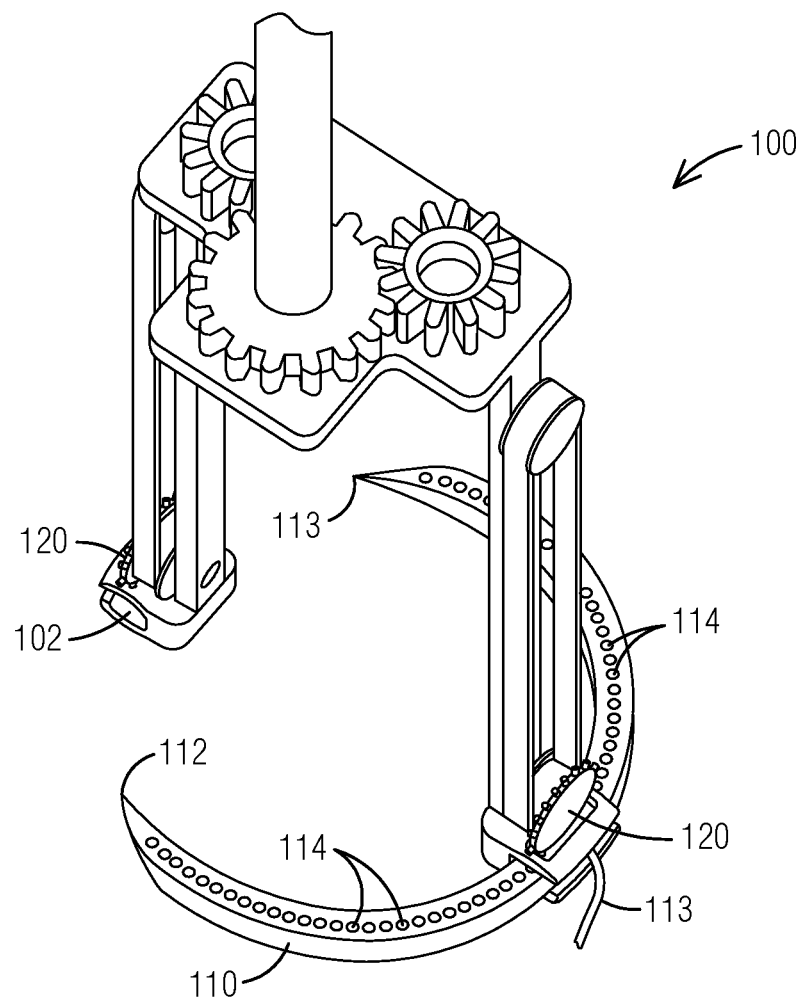
FIG. 8 is a perspective view of a head of a suturing system according to an embodiment disclosed herein.

Referring now to FIG. 7 through FIG. 9, perspective views of a head 100 of a suturing system 1 according to embodiments disclosed herein, are shown. As may be appreciated by those skilled in the art, the exact positioning of the needle 110 with respect to the at least one drive gears 120 and the other elements of the head 100 is non-limiting and may be achieved in a variety of configurations.

As a non-limiting example, in FIG. 7, the head 100 may further include a main belt 810, a transmission gear 820, and a transmission belt 830. As will be discussed in more detail below, the main belt 810 may be driven by a drive mechanism 150, discussed in more detail in the embodiments shown in FIGS. 11-13 and 16. The main belt 810 may then drive the transmission gear 820, which in turn may then drive the transmission belt 830 to control the circular movement of the needle 110. The at least one drive gear 120 and the needle 110 may have the same rotational plane. In a non-limiting embodiment, such as shown in FIG. 8, the at least one drive gear 120 and the needle 110 may have rotational planes that are perpendicular to each other.

Figure 9A:
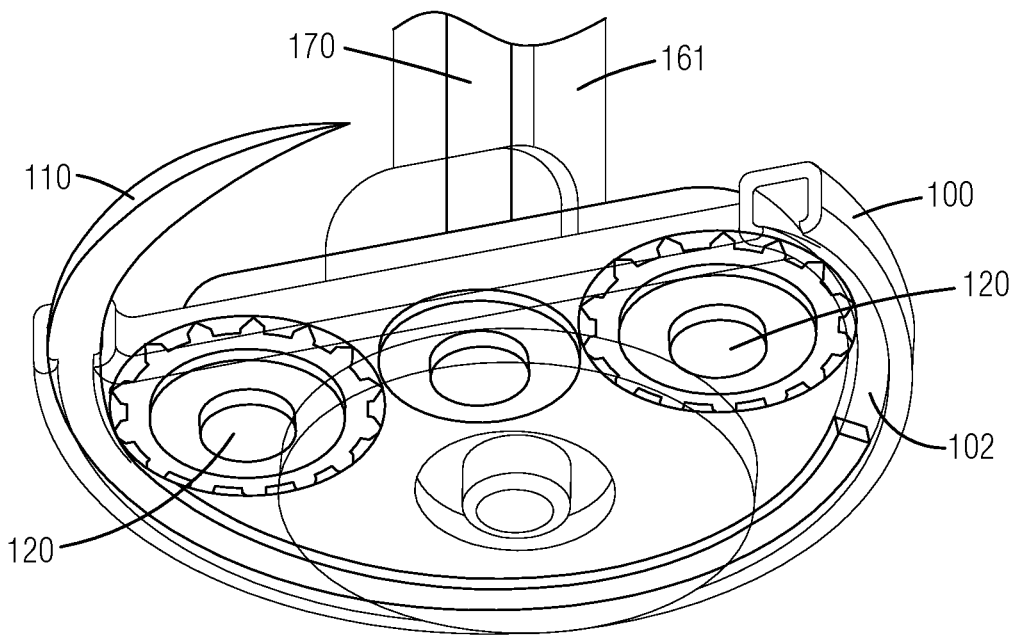
FIG. 9A is a perspective view of a head of a suturing system according to an embodiment disclosed herein.
Figure 9B:
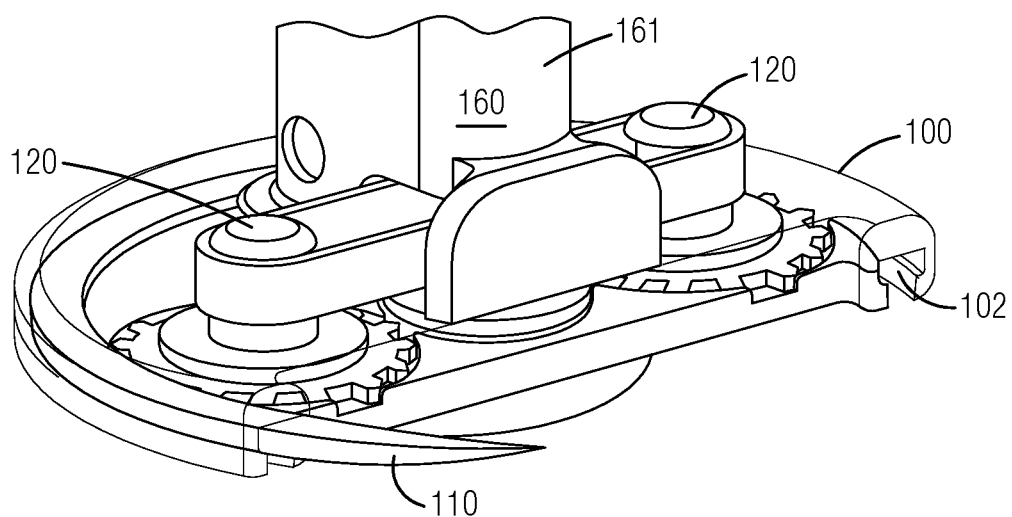
FIG. 9B is another perspective view of the head of the suturing system shown in FIG. 9A, according to an embodiment disclosed herein.

Regarding FIGS. 9A and 9B, perspective views of a head 100 of a suturing system 1 according to embodiments disclosed herein, are shown. As will be discussed in more detail below, the suturing system 1 may include at least one support body 160 and at least one driveshaft 170. In an embodiment, the support body 160 may be an elongated hollow structure to enable the driveshaft 170 to be housed therein and to rotate freely. In an embodiment, the driveshaft 170 may comprise multiple elements mechanically engaged with each other. The driveshaft 170 may be connected on one end to the drive mechanism 150 and on the other end to a main transmission gear 1010 mounted to the head 100. In another embodiment, the main transmission gear 1010 may power the at least one drive gear 120 to enable controlled circular movement of the needle 110. The head 100 may be attached to a distal end 161 of the support body 160.

Figure 10:
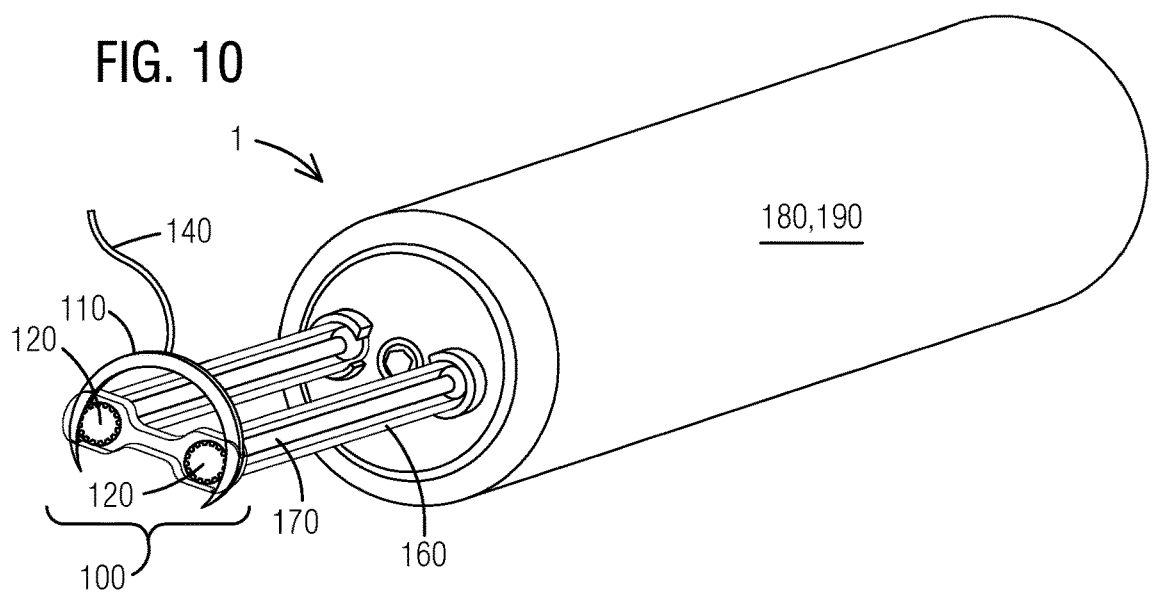
FIG. 10 is a perspective view of a suturing system according to an embodiment disclosed herein.

Referring now to FIG. 10, a perspective view of a suturing system 1 according to an embodiment disclosed herein, is shown. As mentioned above, in an embodiment, the main housing 180 and the handle 190 may be form a single continuous piece. In another embodiment, the at least one support body 160 may extend from the main housing 180 to the head 100. In yet another embodiment, the head 100, the at least one support body 160, and the drive mechanism 150 may be connected to each other as to enable unitary rotation of at least the head 100, the at least one support body 160, and the drive mechanism 150. In another embodiment, the drive mechanism 150 may be secured to the pivot drive mechanism 155 thereby allowing the pivot drive mechanism 155 to rotate the head 100, the at least one support body 160, and the drive mechanism 150.

Figure 11:
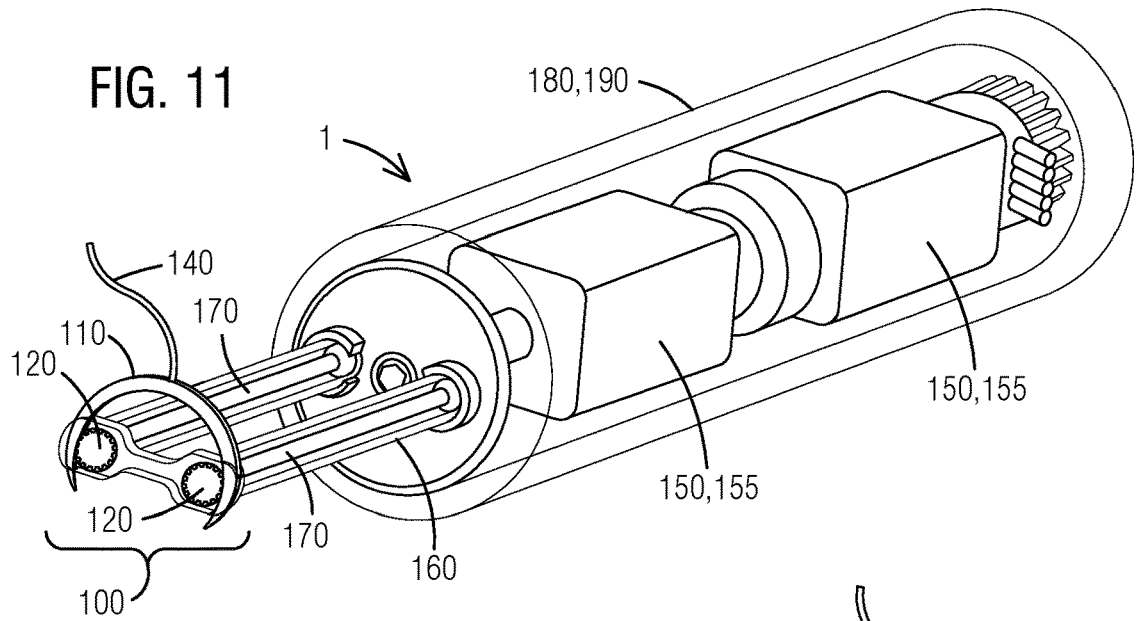
FIG. 11 is another perspective view of the suturing system of FIG. 10, according to an embodiment disclosed herein.
Figure 12:
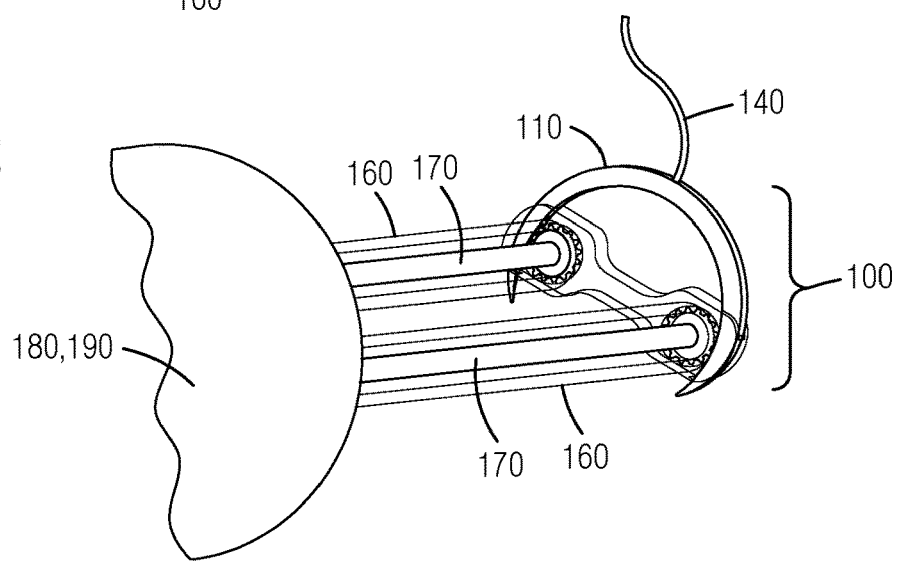
FIG. 12 is a detailed view of the head of the suturing system of FIG. 10, according to an embodiment disclosed herein.

FIG. 11 is a perspective view and FIG. 12 is a detailed view, respectively, of the suturing system 1 of FIG. 10, according to an embodiment disclosed herein. As may be appreciated, the drive mechanism 150 and the pivot drive mechanism 155 may be contained within at least one of the main housing 180 and the handle 190. FIG. 12 shows a detailed view of the head 100 of the suturing system 1 of FIG. 15, according to an embodiment disclosed herein.

In some embodiments, at least one of the drive mechanism 150 and the pivot drive mechanism 155 may be controllable by a user. As discussed in more detail below, in some non-limiting embodiments, at least one of the drive mechanism 150 and the pivot drive mechanism 155 may be controlled with at least one of the drive input 151 and the pivot input 157 to change at least one of a rotational speed, a number steps, and the torque applied by at least one of the drive mechanism 150 and the pivot drive mechanism 155.

Figure 15:
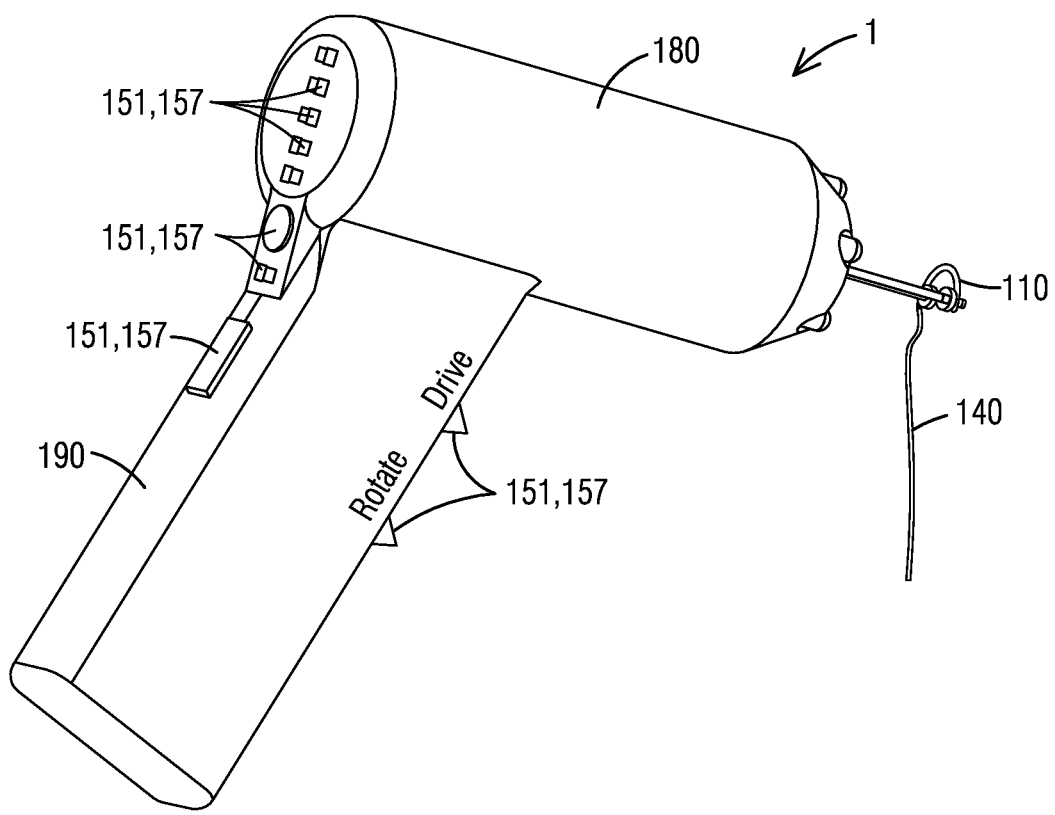
FIG. 15 is a perspective view of a suturing system according to an embodiment disclosed herein.

Referring now to FIGS. 13A-13K, detailed views of the rotation of the needle 110 and head 100 of the suturing system 1 of FIG. 15, according to an embodiment disclosed herein, are shown. Specifically, FIGS. 13A-13D illustrate counterclockwise movement of the needle 110 with respect to the head 100. As may be appreciated, the needle 110 may rotate an infinite number of revolutions in either direction. In an embodiment, the user may rotate the needle 110 by controlling the drive input 151.

Figure 13A:
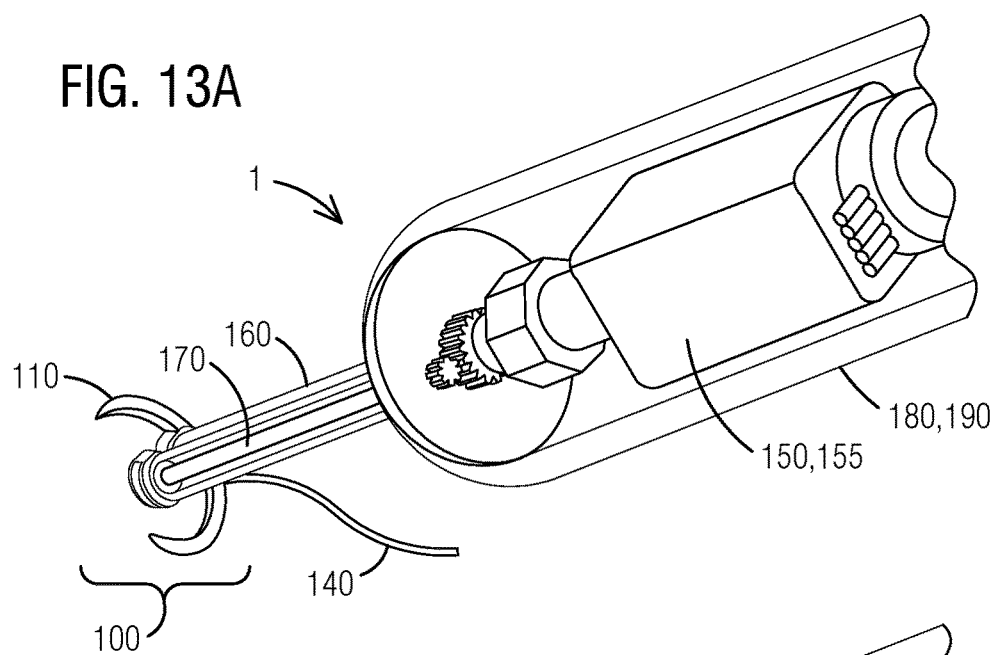
FIGS. 13A-13K are detailed views of the operation of the head of the suturing system of FIG. 10, according to an embodiment disclosed herein.
Figure 13B:
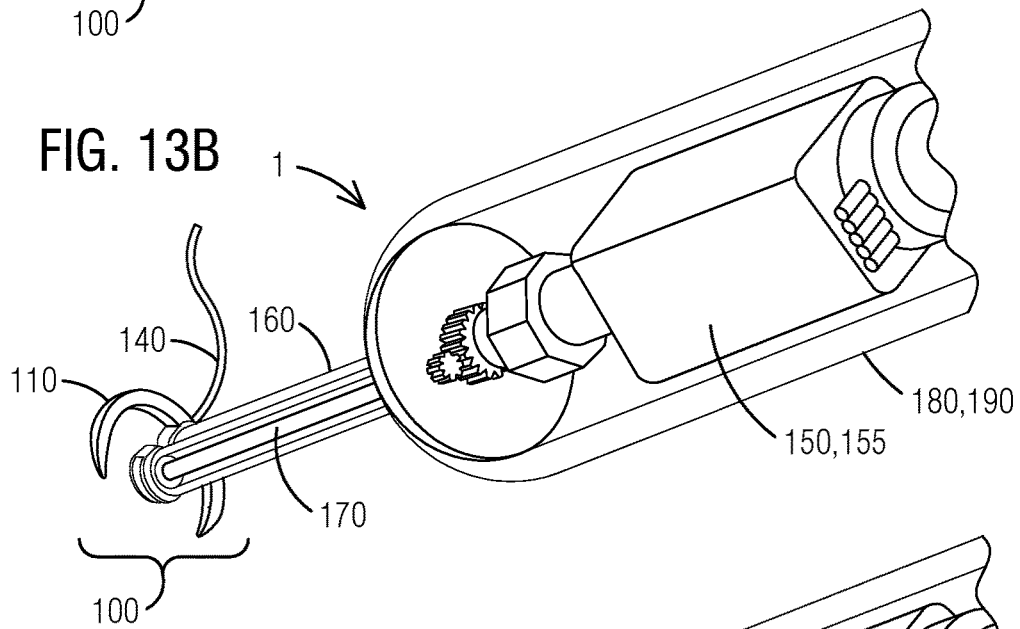
Figure 13C:
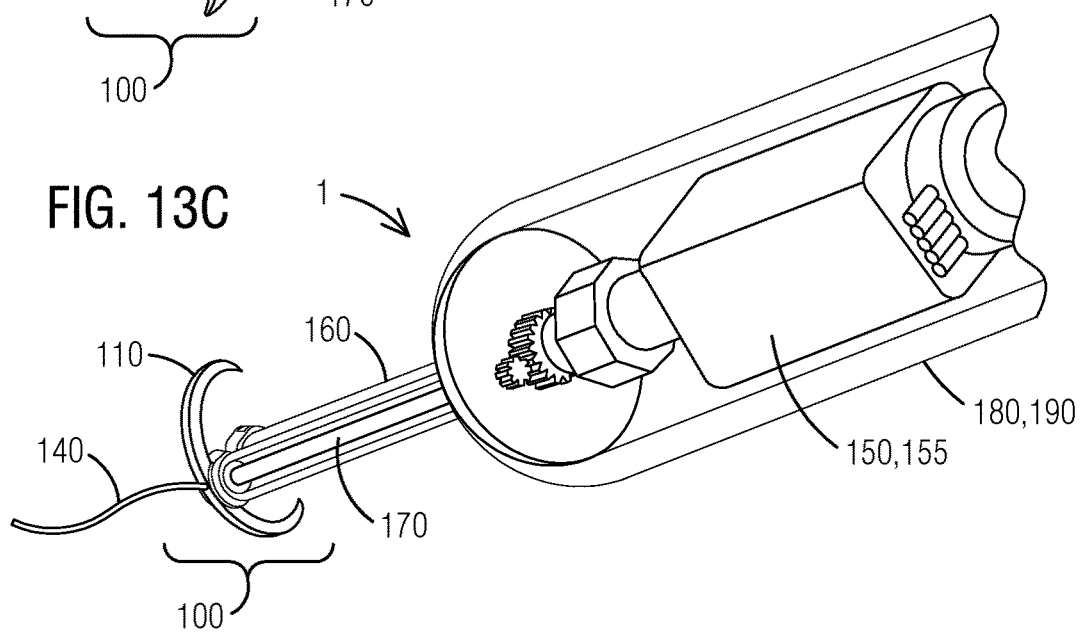
Figure 13D:
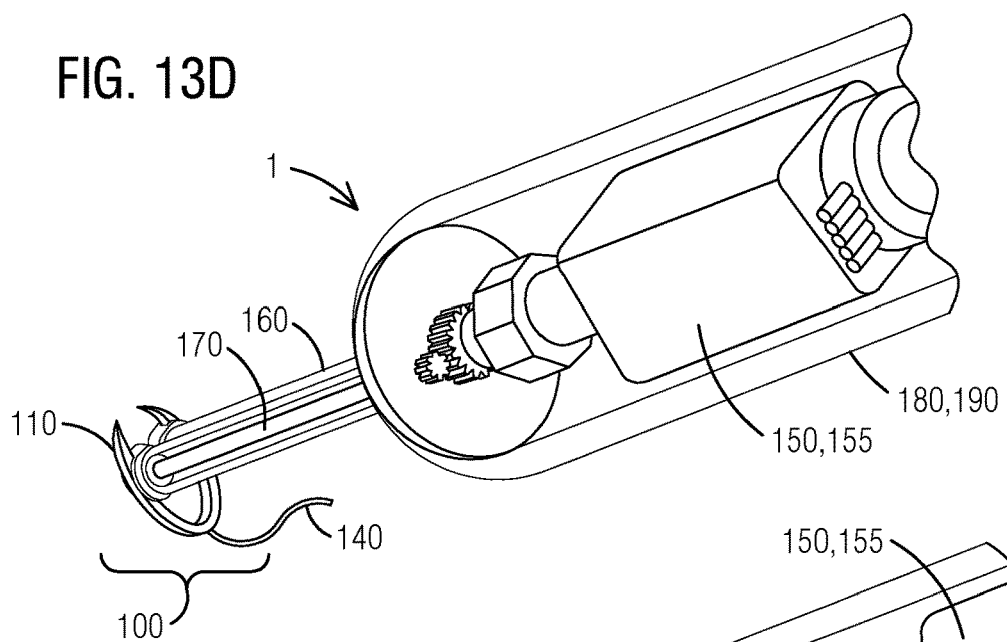
Figure 13E:
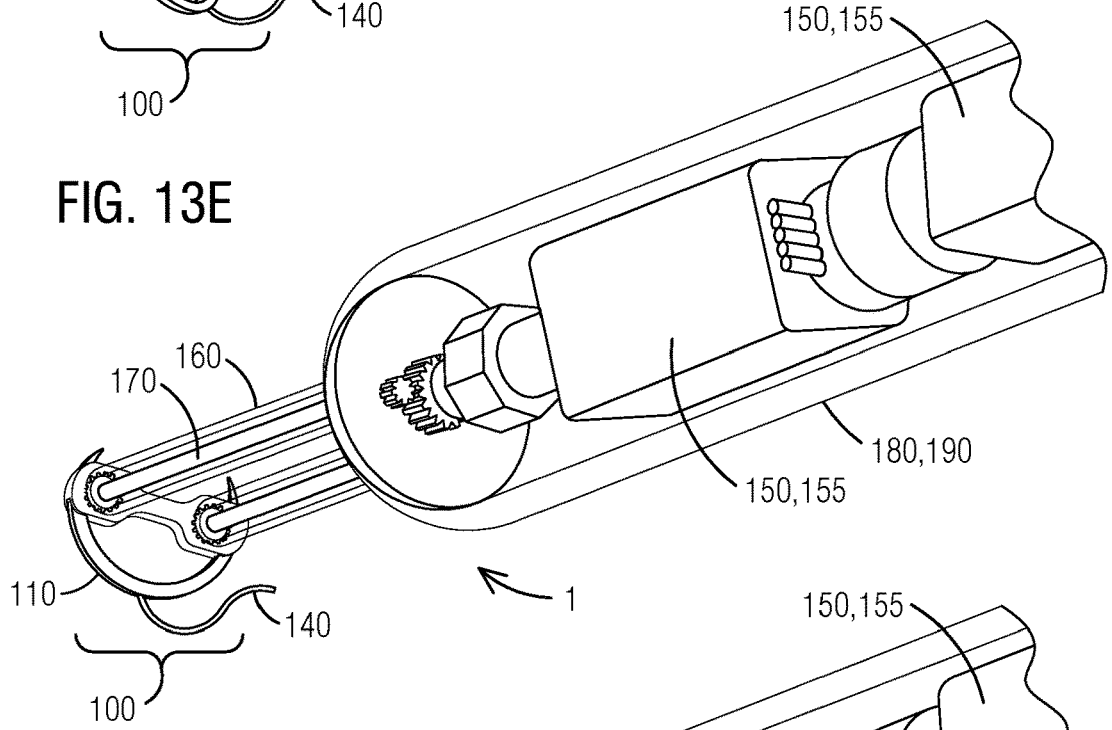
Figure 13F:
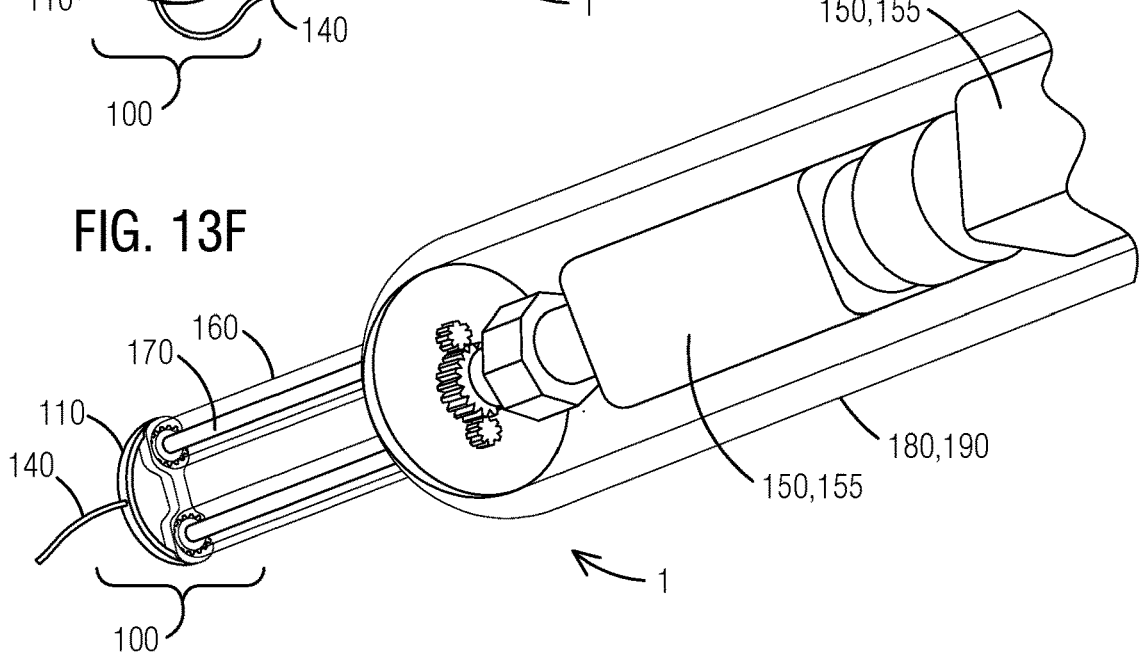
Figure 13G:
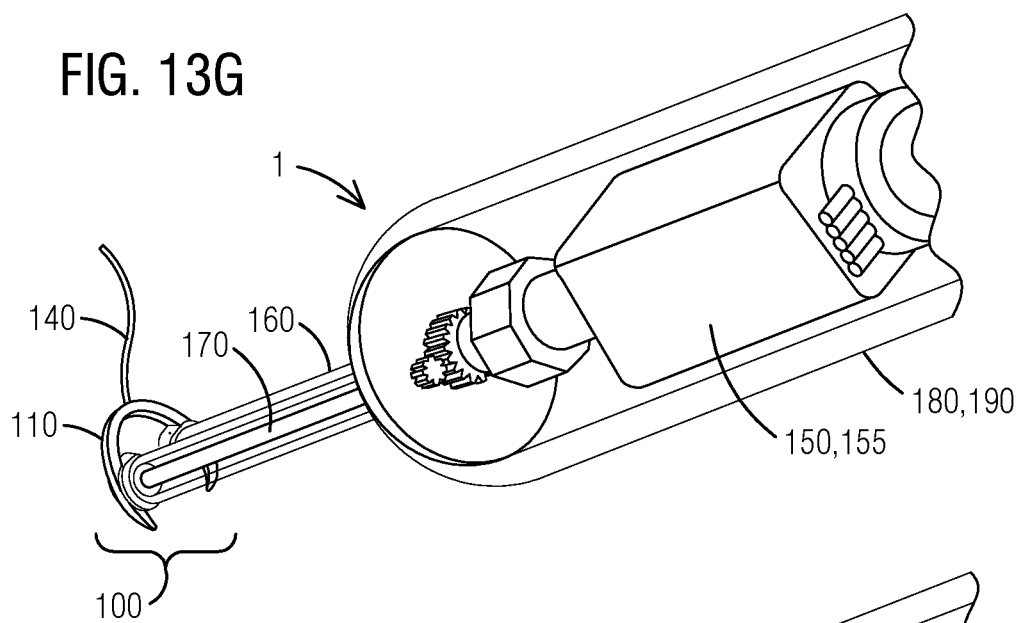
Figure 13H:
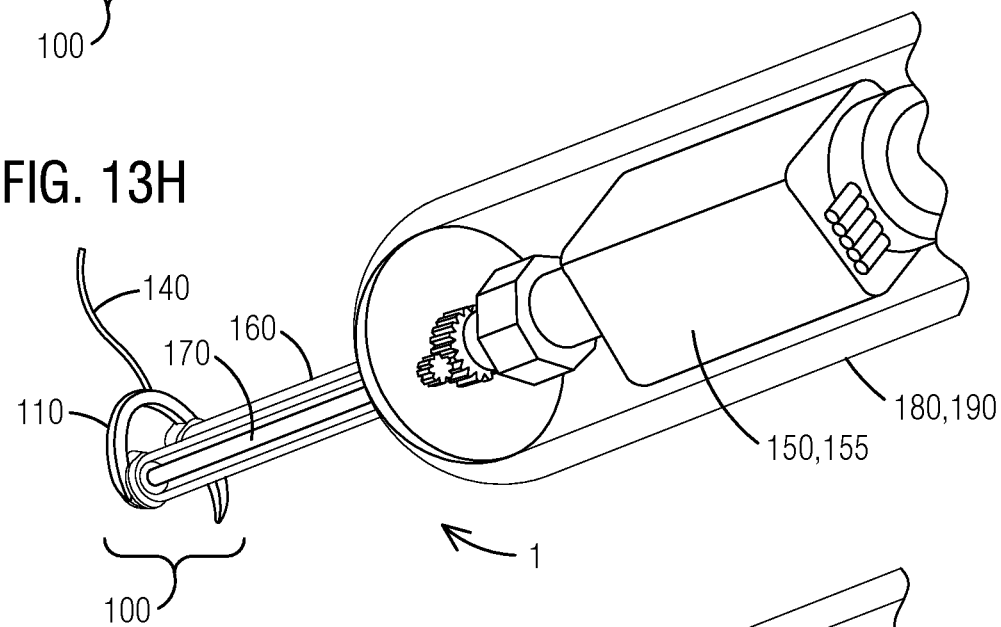
Figure 13I:
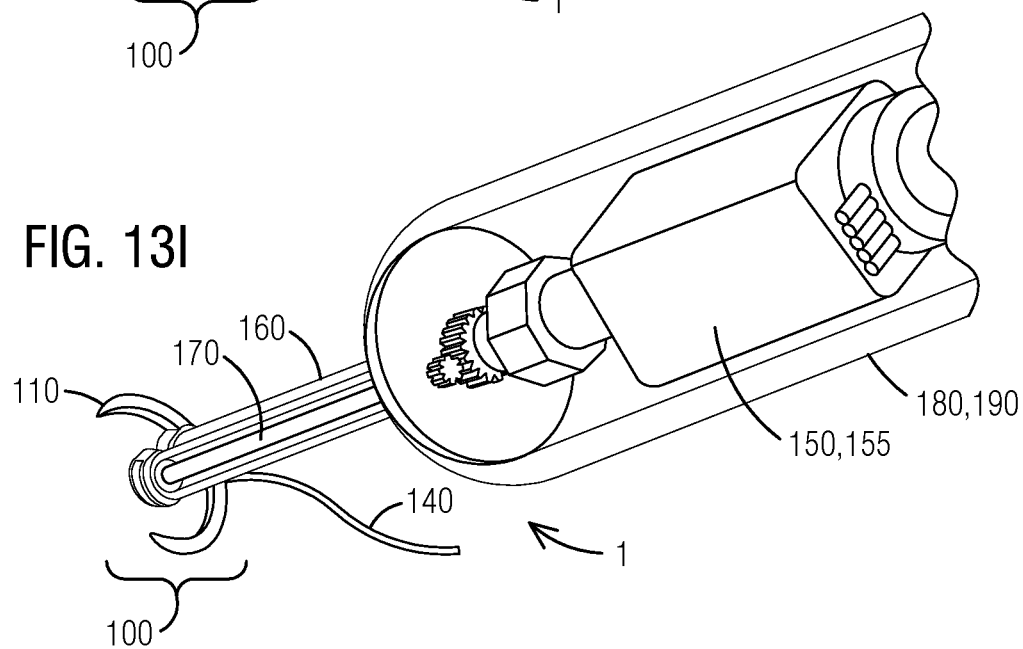
Figure 13J:
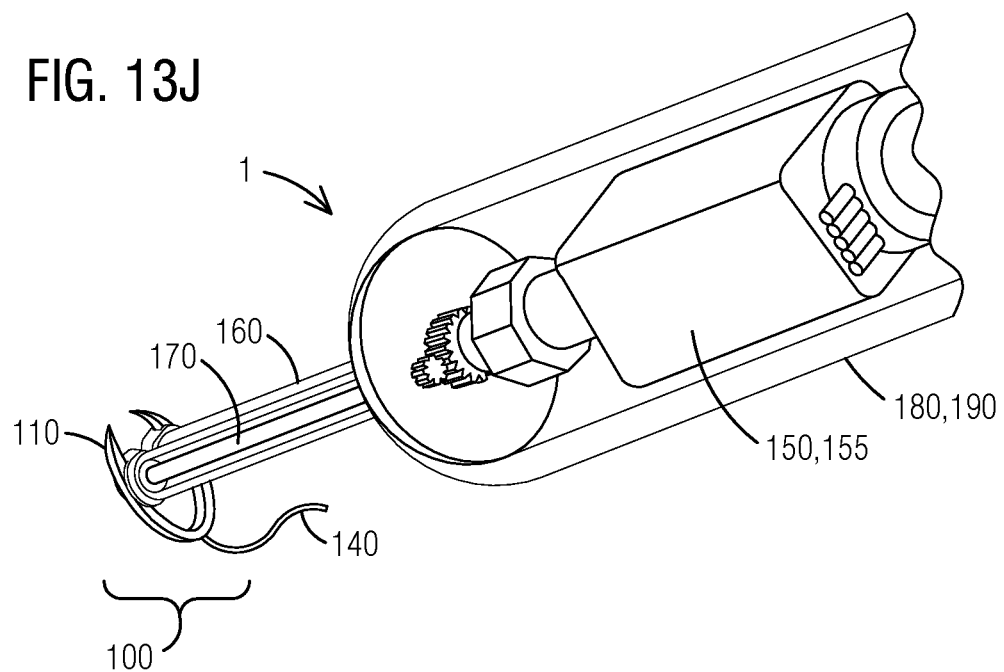
Figure 13K:
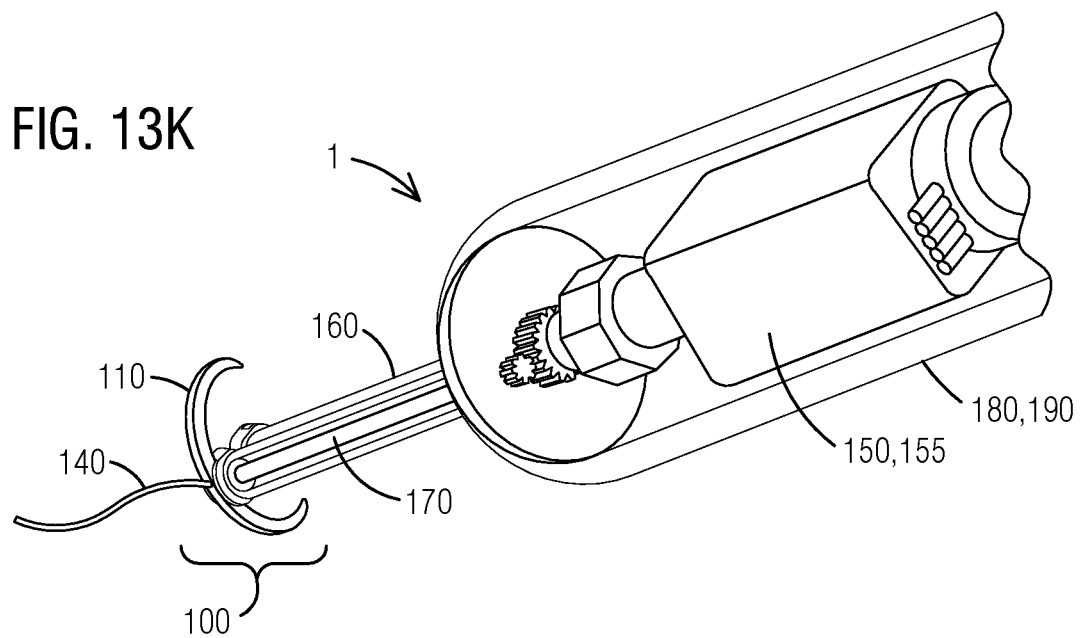

FIGS. 13E-13G illustrate the clockwise rotation of at least one of the head 100, the at least one support body 160, and the drive mechanism 150, according to an embodiment. As may be appreciated, an infinite number of revolutions of the at least one of the head 100, the at least one support body 160, and the drive mechanism 150 may be achieved by methods known in the art. In an embodiment, the user may rotate the head 100 by controlling the pivot input 157.

FIGS. 13H-13K illustrate the clockwise rotation of the needle 110 with respect to the head 100, according to an embodiment. As previously discussed, the needle 110 may rotate an infinite number of revolutions in either direction.

Figure 14A:
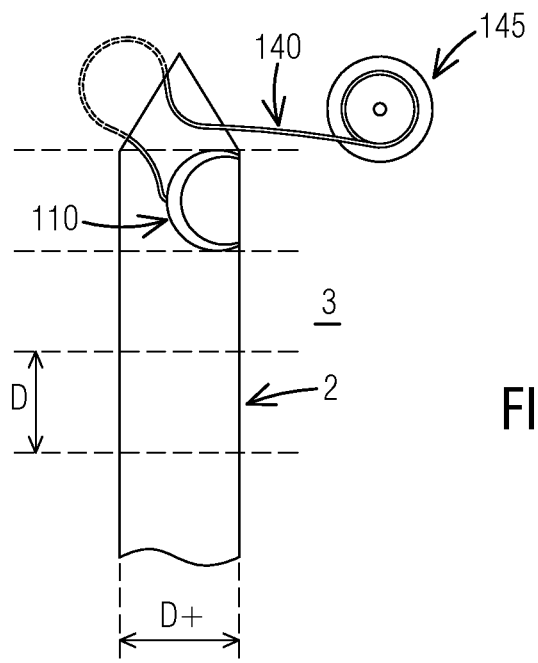
FIGS. 14A-14E are detailed views of a non-limiting stitch that may be effected by the suturing system of FIG. 10, according to an embodiment disclosed herein.
Figure 14B:
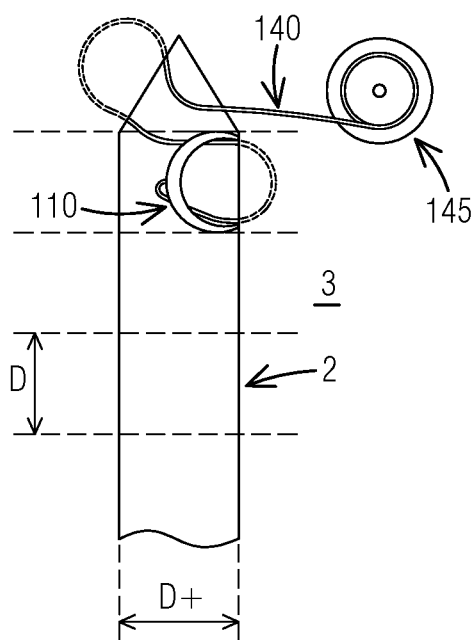

FIGS. 14A-14E are detailed views of a non-limiting subcuticular running stitch 2 that may be effected by the suturing system 1 of FIG. 10, according to an embodiment disclosed herein. FIGS. 14A-14E illustrate a non-limiting subcuticular running stitch 2 accomplished by the operation of the non-limiting embodiments of the suturing system 1 described in FIGS. 13A-13K. As a non-limiting example, FIG. 14A illustrates the position of the needle 110 with respect to the biological material 3 after, first, one counterclockwise rotation of the needle 110 through the biological material 3 as illustrated in FIGS. 13A-13D to pull the suture 140 through the biological material 3 and, then, the clockwise rotation of at least one of the head 100, the at least one support body 160, and the drive mechanism 150 as illustrated in FIGS. 13E-13G. FIG. 14B illustrates the position of the needle 110 with respect to the biological material 3 after a clockwise rotation of the needle 110 through the biological material 3 as illustrated in FIGS. 13H-13K to pull the suture 140 through the biological material 3.

Figure 14C:
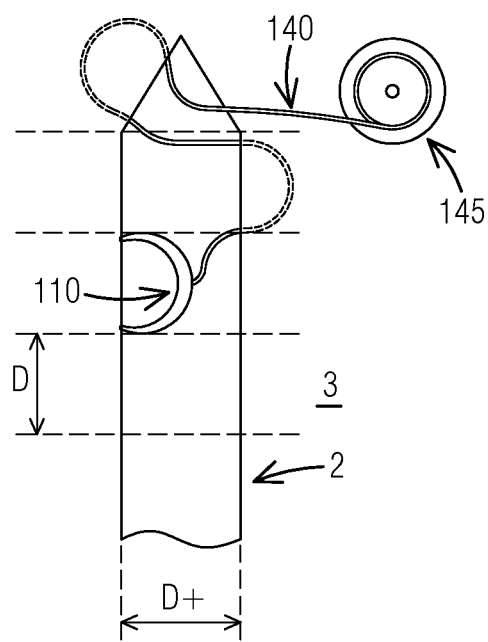
Figure 14D:
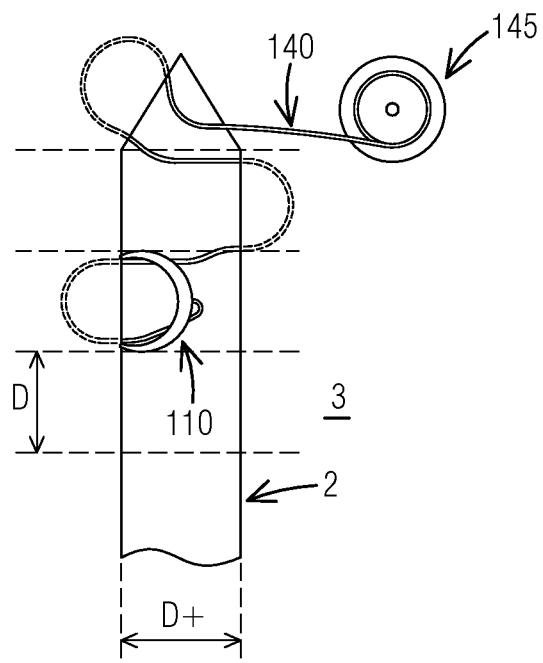
Figure 14E:
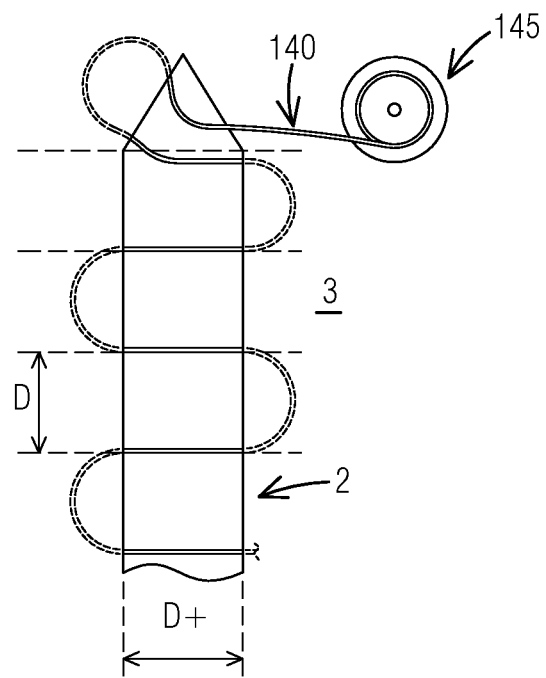

FIGS. 14C and 14D show the operation described in FIGS. 14A and 14B as repeated throughout the wound. FIG. 14E is a non-limiting example of the subcuticular running stitch 2 as accomplished with the suturing system 1 of FIG. 10. It may be noted that FIGS. 14A-14E illustrate only a non-limiting example of a stitch 2 that may be applied with embodiments described herein but that many other types of stitches may be applied with the embodiments described herein. As may be appreciated by those skilled in the art, the references "D" and "D+" in FIGS. 14A-14E and 18A-18D (discussed in further detail below) may indicate a dimension of at least one of the needle 110, the stitch 2, and the biological material 3.

Figure 16:
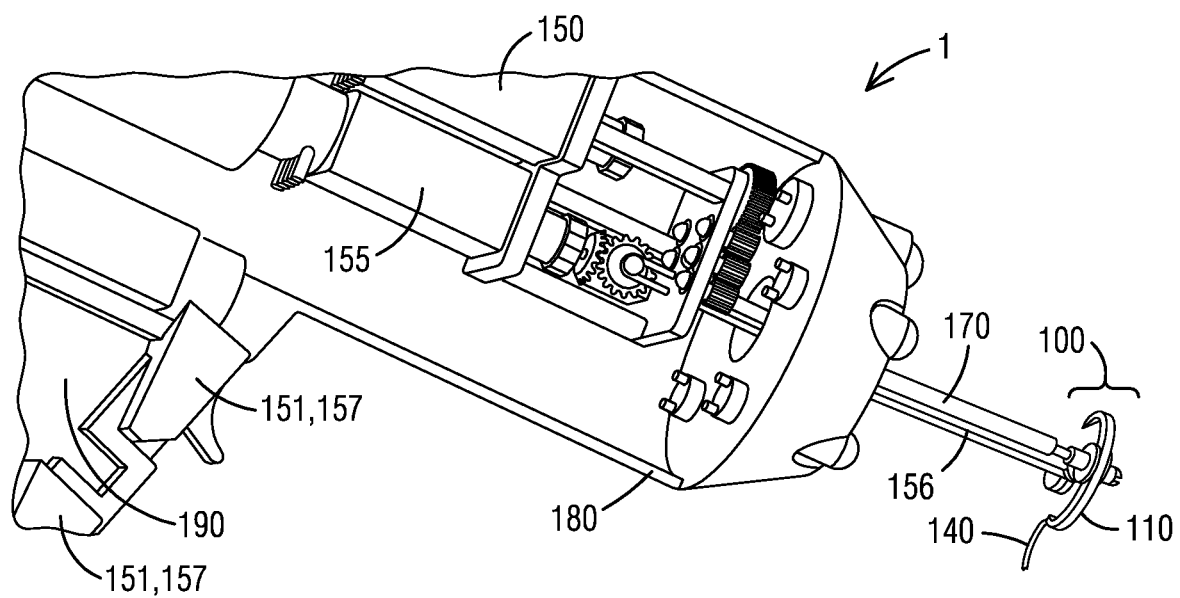
FIG. 16 is a detailed view of the suturing system of FIG. 15, according to an embodiment disclosed herein.
Figure 17A:
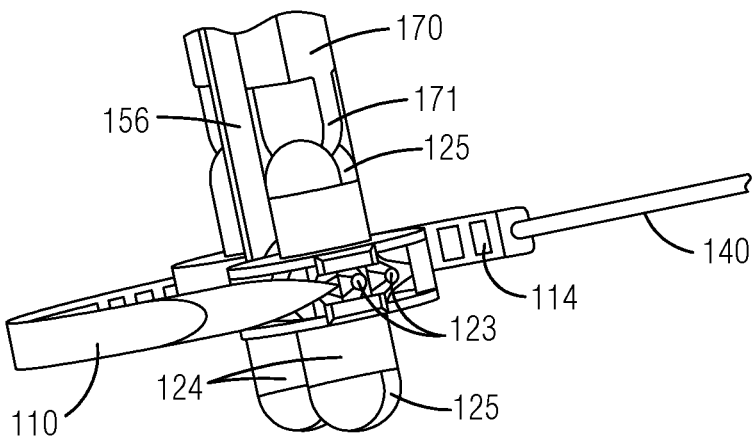
FIGS. 17A-17E are detailed views of the operation of the head of the suturing system of FIG. 15, according to an embodiment disclosed herein.
Figure 17B:
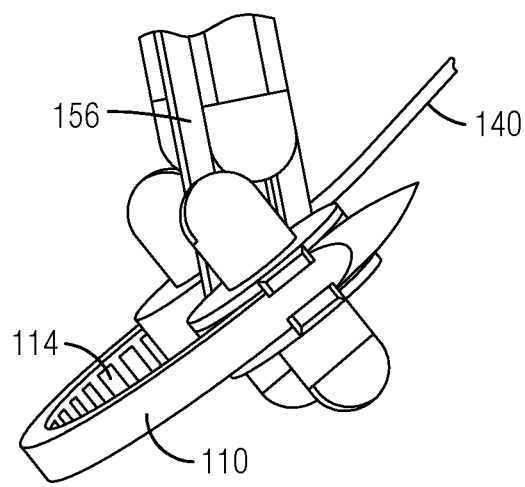
Figure 17C:
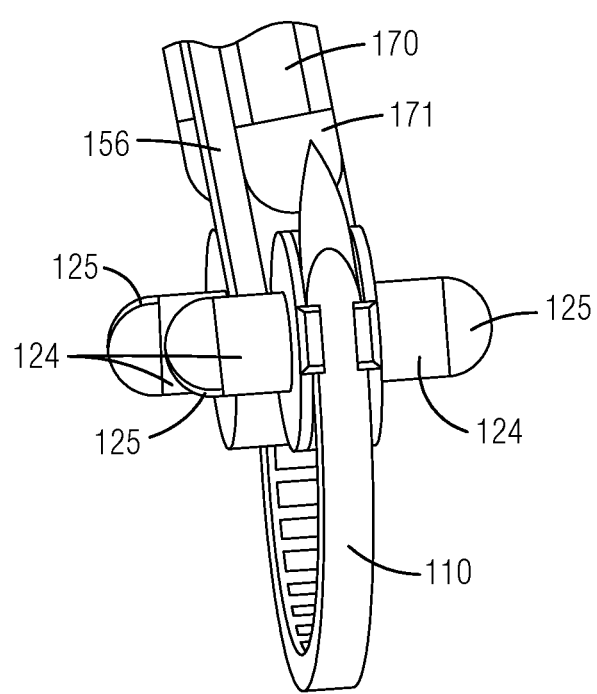
Figure 17D:
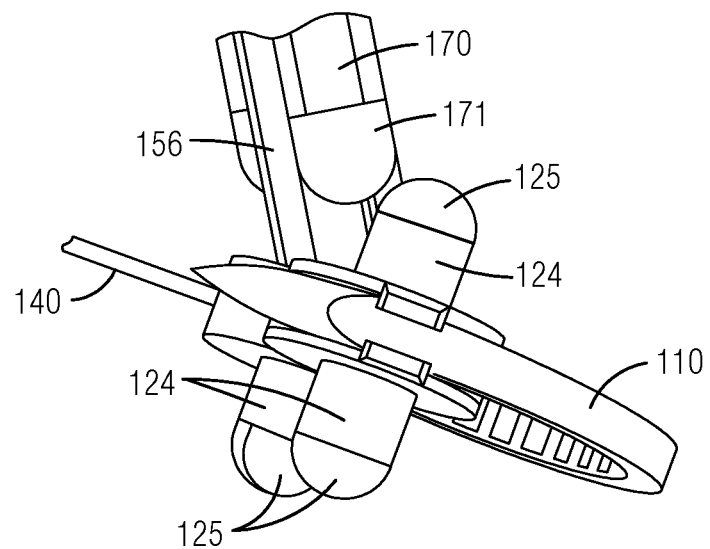
Figure 17E:
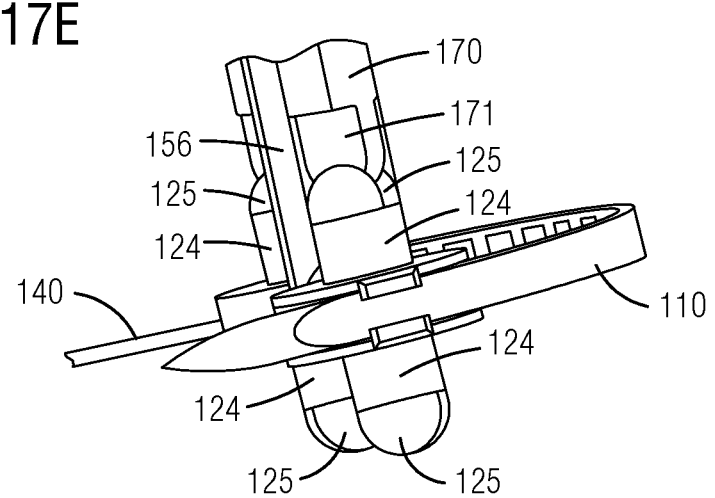

Referring now to FIGS. 15 and 16, a perspective view and a detailed view, respectively, of a suturing system 1 according to an embodiment disclosed herein, are shown. The suturing system 1 may comprise a main housing 180 and a handle 190. In some embodiments, the main housing 180 and the handle 190 may be arranged in a pistol grip configuration. In other embodiments, the main housing 180 and the handle 190 may form a with a continuous elongated piece as shown in the non-limiting embodiment of FIGS. 10-13. In an embodiment, the handle 190 may pivot in relation to the main housing 180. In those embodiments, the angle of the handle 190 with respect to the main housing 180 may be adjustable to reflect the preference of a user.

As may be appreciated in FIGS. 17A-17E (illustrating in more detail the non-limiting embodiment of FIGS. 15 and 16) the suturing system 1 may include a head 100 rotatably mounted perpendicular to a distal end 161 of a support body 160. Rotation of the head 100 may be effected by a pivot drive mechanism 155 including a belt 156, whereby activating the pivot drive mechanism 155 causes the head 100 to rotate about an axis perpendicular to the longitudinal axis of the support body 160. The proximate end 162 of the support body 160 may be mechanically attached to the main housing 180. The drive mechanism 150 and part of the pivot drive mechanism 155 may be housed inside the main housing 180.

In another embodiment, the at least one driveshaft 170 may include one end connected to the drive mechanism 150 and another end having an engaging portion 171. In those embodiments, the at least one drive gear 120 includes a through axle 124 with at least one engaged portion 125 for mating with the engaging portion 171 of the driveshaft 170.

In an embodiment, rotation of the needle 110 is achieved by the operation of the drive mechanism 150. In another embodiment, the drive mechanism 150 may include a drive input 151 to control operation of the drive mechanism 150. In another embodiment, operation of the drive input 151 by the user determines the rotational speed and direction of the needle 110. In yet another embodiment, predetermined parameters entered into the drive input 151 may the rotational speed and direction of the needle 110. As it may be appreciated, the needle 110 may be rotated either clockwise or counterclockwise at any speed and for any number of turns. In another embodiment still, the needle 110 may rotate in discrete steps. In yet another embodiment, the user may select at least one of the number of steps, rotational speed, and torque.

In an embodiment, rotation of the head 100 is achieved by the operation of the pivot drive mechanism 155. In other embodiments, the pivot drive mechanism 155 may include a pivot input 157 to control operation of the pivot drive mechanism 155. In some other embodiments, operation of the pivot input 157 by the user determines the rotational speed and direction of the head 100. In some other embodiments still, predetermined parameters entered into the pivot input 157 may the rotational speed and direction of the head 100. As it may be appreciated, the head 100 may be rotated either clockwise or counterclockwise at any speed and for any number of turns. In other embodiments, the head 100 may rotate in discrete steps. In some other embodiments, the user may select at least one of the number of steps, rotational speed, and torque.

As may be further appreciated by those skilled in the art, the arrangement of the drive mechanism 150 and the pivot drive mechanism 155 is non-limiting and may be achieved in a multitude of ways. As a non-limiting example, the drive mechanism 150 and the pivot drive mechanism 155 may share at least one of mechanical elements and electrical elements. In an embodiment, the drive mechanism 150 and the pivot drive mechanism 155 are the same system. In another embodiment, the drive input 151 and the pivot input 157 may share at least one of mechanical elements and electrical elements. In other embodiments, the drive input 151 and the pivot input 157 may be the same.

In an embodiment, the drive mechanism 150 and the pivot drive mechanism 155 may comprise at least one of a stepper motor, a servo motor, a brushless motor, a direct current (DC) motor, a microgear DC motor, a microgear DC motor with an encoder, and an alternative current (AC) motor. In another embodiment, the drive mechanism 150 and the pivot drive mechanism 155 may comprise at least one of digital circuitry or analog circuitry.

In another embodiment, the drive input 151 and the pivot input 157 may comprise at least one of pedals, triggers, buttons, switches, touch screens, digital displays, analog displays, holographic headsets, voice recognition, microphones, haptic sensors, accelerometers, gyroscopes, cameras, infrared sensors, sonar sensors, and laser sensors.

In yet some other embodiments, the suturing system 1 may be a completely automated or autonomous system. In those embodiments, a suite of sensors, including but not limited to accelerometers, gyroscopes, cameras, infrared sensors, sonar sensors, and laser sensors, in conjunction with a processor and memory, including a software component, may determine and control the required pathways and operations to be effected on the drive input 151, the pivot input 157, and the corresponding drive mechanism 150 and pivot drive mechanism 155 to achieve a stitch 2 on the biological material 3. Further, in those embodiments, the suturing system 1 may at least on of scan, measure, and map the biological material 3 (using the suite of sensors) to determine the best pathway for the suture 140 and then operate at least one of the drive input 151, the pivot input 157, the drive mechanism 150, and the pivot drive mechanism 155.

Returning now to FIGS. 17A-17E, it may be noted, when a rotational plane of the needle 110 in the head 100 is perpendicular to the support body 160, the at least one engaged portion 125 may be in contact with the engaging portion 171 of the driveshaft 170, wherein rotation of the driveshaft 170 by the drive mechanism 150 causes rotation of the needle 110. In another embodiment, rotation of the head 100 by the pivot drive mechanism 155 may cause the at least one engaged portion 125 to become disengaged with the engaging portion 171 of the driveshaft 170.

Figure 18A:
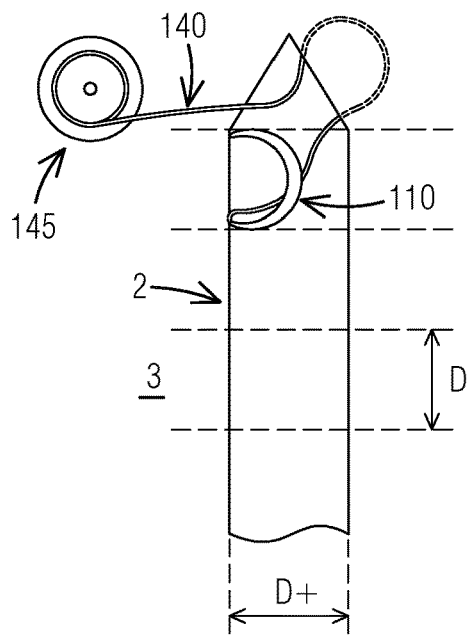
FIGS. 18A-18D are detailed views of a non-limiting stitch that may be effected by the suturing system of FIG. 15, according to an embodiment disclosed herein.

FIGS. 18A-18D are detailed views of a non-limiting example stitch 2 that may be effected by the suturing system 1 of FIG. 15, according to an embodiment disclosed herein. In an embodiment, FIGS. 18A-18D illustrate a subcuticular running stitch 2 accomplished by the operation of the non-limiting embodiment of the suturing system 1 described in FIGS. 17A-17E. FIG. 18A illustrates the position of the needle 110 with respect to the biological material 3 after, first, one clockwise rotation of the needle 110 through the biological material 3 to pull the suture 140 through and, then, the rotation of the head 100 by the pivot drive mechanism 155 as illustrated in FIGS. 17A-17E to position the needle 110 to face the opposite side of the wound.

Figure 18B:
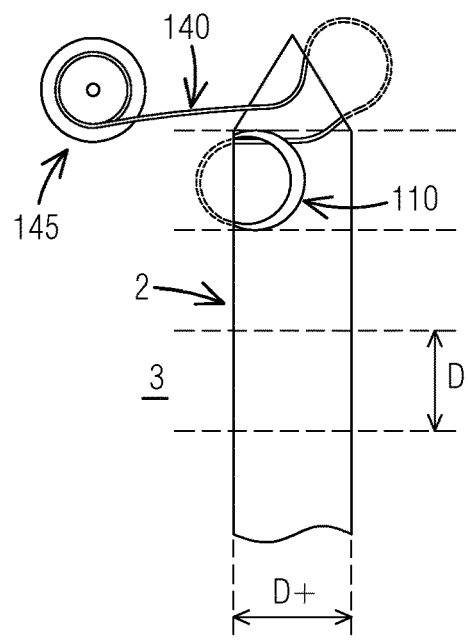
Figure 18C:
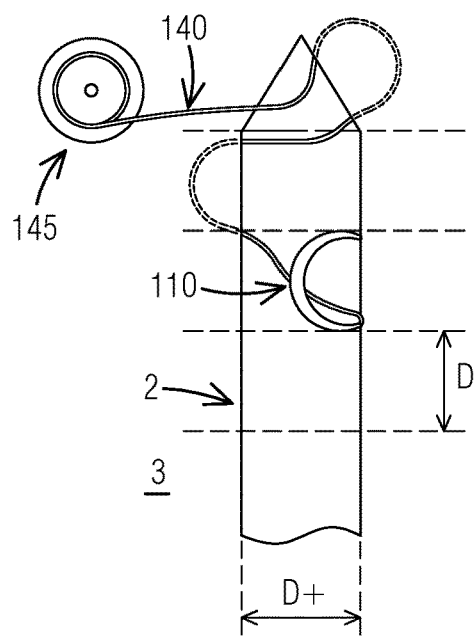
Figure 18D:
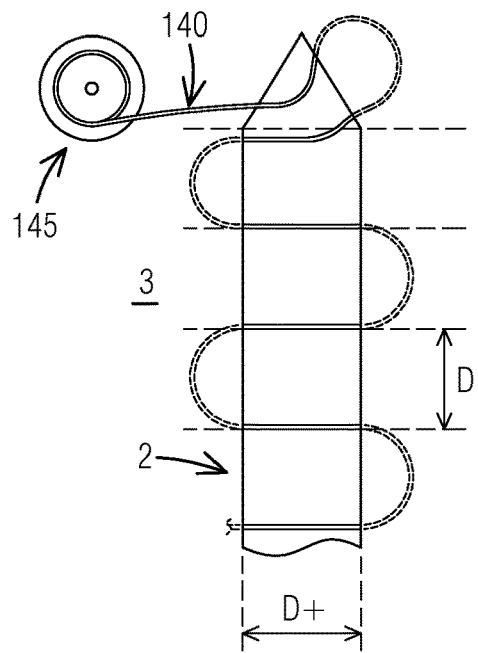

FIGS. 18B and 18C show the operation described in FIG. 14A as repeated throughout the wound. FIG. 14D is a non-limiting example of the subcuticular running stitch 2 as accomplished with the suturing system 1 of FIG. 15. As mentioned above, it may be noted that FIGS. 18A-18D illustrate only a non-limiting example of a stitch 2 that may be applied with embodiments described herein but that many other types of stitches may be applied.

Referring now to FIGS. 19 and 20, a perspective view and a detailed view, respectively, of a suturing system 1, according to an embodiment disclosed herein, are shown. As previously discussed, the main housing 180 may pivot with respect to the handle 190. As may be appreciated by those skilled in the art, configuration and arrangement of the head 100, support body 160, and needle 110 are non-limiting and may be achieved in a multitude of ways.

Figure 21:
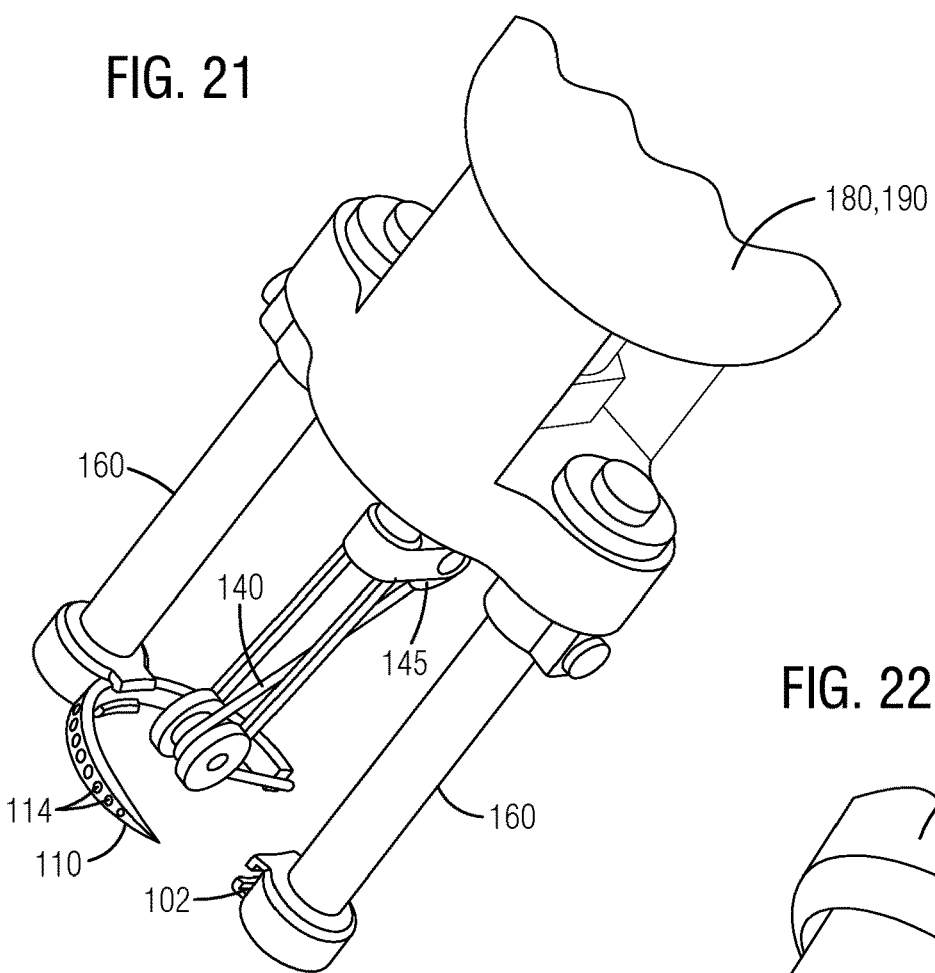
FIG. 21 is a perspective view of a head of a suturing system according to an embodiment disclosed herein.
Figure 22:
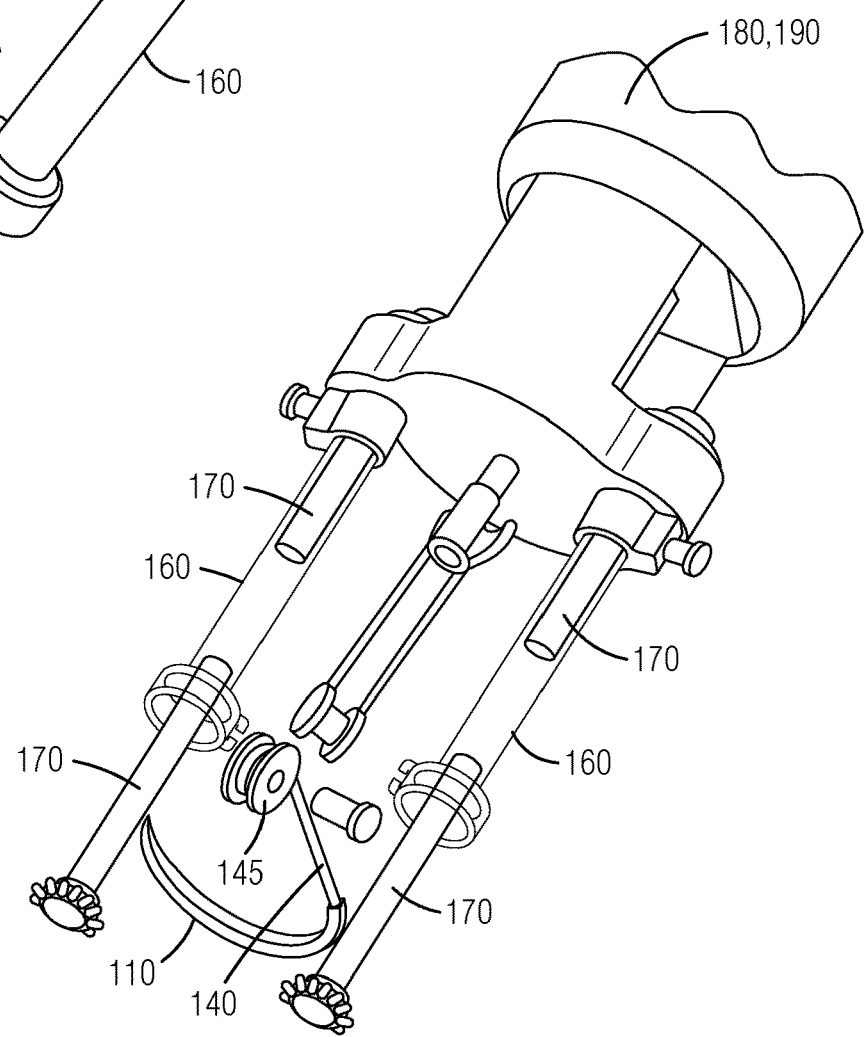
FIG. 22 is an exploded view of the head of the suturing system of FIG. 21, according to an embodiment disclosed herein.
Figure 23:
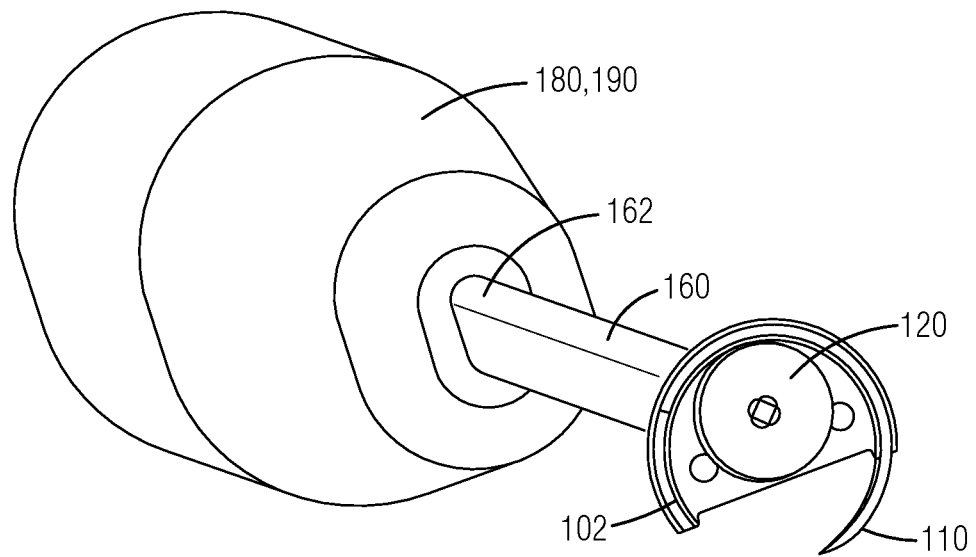
FIG. 23 is a perspective view of a head of a suturing system according to an embodiment disclosed herein.

Referring now to FIGS. 21 and 22, a perspective view and an exploded view of a head 100 of a suturing system 1, according to embodiments disclosed herein, are shown. In an embodiment, the head 100 may include a spool 145. In an embodiment, the suture 140 may be wound around the spool 145. In another embodiment, the spool 145 may rotate in conjunction with the needle 110 and the suture 140 may pay out as the needle 110 is rotated by the drive gears 120.

In another embodiment, the spool 145 may be attached to a portion of the biological material 3 near a starting position of the stitch 2 and may unwind as additional stitches are applied to the biological material 3. The non-limiting examples shown in FIGS. 14A-14E and 18A-18D illustrate the spool 145 secured to the biological material 3. In some embodiments, the spool 145 may be secured to the biological material 3 by at least one of stapling, pinning, bonding, gluing, and stitching.

As may be noted by those skilled in the art, the final step in applying a subcuticular continuous stitch 2 is a below surface tie off procedure on both ends of the stitch 2. In some embodiments disclosed herein, this is easy to accomplish on the last perforation of the biological material 3 by disengaging and removing the needle 110 from the head 100, thus allowing for the separation of the suture 140 from the needle 110 (in other embodiments the suture 140 may be separated from the needle 110 without removing the needle 110 from the head 100). Subsequently, the suture 140 may be pulled to further tighten the stitch 2 and tie the suture 140 off. In some embodiments, the tie off may be achieved using the needle 110 by applying traditional suturing hand methodology. However, as it may be appreciated, the end where the initial perforation is made involves additional challenges since in some embodiments there is no needle 110 on that end and the thread is longer than is needed to complete the continuous stitch 2. Therefore, with some of the non-limiting embodiments disclosed herein, advantages accrue when having the spool 145 secured to the biological material 3 and a second needle 110 is contained within the spool 145 so that a tie off may be achieved.

Referring now to FIGS. 23 through 26, perspective views of a head 100 of a suturing system 1 according to embodiments disclosed herein, are shown. As may be appreciated by those skilled in the art, FIGS. 23 through 26 illustrate that the elements described herein may be arranged in a multitude of non-limiting configurations.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

We claim:

1. A suturing system, comprising:
   at least one drive gear with a plurality of outward protrusions; and
   a needle with a first end, a second end, and a plurality of indentations therebetween;
   at least one driveshaft with opposing ends;
   a drive mechanism connected to the drive gear by way of the at least one driveshaft connected to the drive mechanism at a first opposing end and the at least one driveshaft connected to the drive gear at a second opposing end;
   at least one support body, the at least one support body comprises a proximate end and a distal end; and
   a head mounted on the at least support body and perpendicular to the distal end of the at least one support body;
   wherein the plurality of indentations engage with the plurality of outward protrusions of the drive gear to circularly rotate the needle;
   wherein the at least one drive gear rotates with the needle; and
   wherein a rotational plane of the needle is perpendicular to the support body.

2. The suturing system of claim 1, wherein the drive mechanism is at least one of a stepper motor, a servo motor, a brushless motor, and a microgear DC motor with an encoder.

3. The suturing system of claim 1, wherein the first end comprises a pointed end of the needle to penetrate a biological material.

4. The suturing system of claim 3, wherein the second end of the needle comprises a pointed end to penetrate the biological material.

5. The suturing system of claim 1, further comprising a suture connected to the needle.

6. The suturing system of claim 5, wherein the needle further comprises an attachment point located between the first end and the second end, and wherein the suture is connected to the needle on at least one of the first end, the second end, and the attachment point.

7. The suturing system of claim 1, wherein the needle comprises an arcuate shape with a contacting surface, and wherein the plurality of indentations is provided in a repetitive machine pattern in the contacting surface.

8. The suturing system of claim 1, wherein the needle comprises at least one of a toroidal helix shape and a cylindrical helix shape, the at least one of the toroidal helix shape and the cylindrical helix shape comprise a contacting surface, and wherein the plurality of indentations are a repetitive machine pattern on the contacting surface.

9. The suturing system of claim 1, further comprising a handle, wherein the drive mechanism is mounted to the handle.

10. The suturing system of claim 1, further comprising a removable suture spool attached to at least one of the handle and a biological material, and a suture wound around the removable suture spool; the suture connected to the needle.

11. The suturing system of claim 10, wherein the needle further comprises an attachment point between the first end and the second end, and wherein the suture is connected to the needle at least one of the first end, the second end, and the attachment point.

12. The suturing system of claim 1, further comprising a suture connected to the needle, the needle comprising an attachment point between the first end and the second end, and wherein the suture is connected to the needle on at least one of the first end, the second end, and the attachment point.

13. The suturing system of claim 1, wherein the at least one drive gear is mounted to the head and rotates with the head.

14. A suturing system, comprising:
    a handle;
    a drive mechanism mounted to the handle;
    a support body having a proximate end and a distal end, the proximate end connected to the handle;
    a head rotatably mounted on the distal end of the support body, whereby the head rotates perpendicular to the longitudinal axis of the support body;
    a pivot drive mechanism connected to the head on one end and to the handle on the other, wherein the pivot drive mechanism causes the head to rotate;
    at least one drive gear with a plurality of radially mounted outward protrusions and a through axle with opposing ends, each opposing end having an engaged portion, the at least one drive gear mounted to the head;
    at least one driveshaft with a driven end and an engaging end, the driven end connected to the drive mechanism, and the engaging end in mating contact with the engaged portion of the at least one gear; and
    a needle with a first end, a second end, and a plurality of indentations therebetween, wherein the plurality of indentations engages with the plurality of outward protrusions of the drive gear to rotate the needle in a circular manner; and
    wherein a rotational plane of the needle in the head is perpendicular to the support body.

15. The suturing system of claim 14, wherein the needle comprise an arcuate shape with a contacting surface; and wherein the plurality of indentations are a repetitive machine pattern on the contacting surface.

16. The suturing system of claim 15, further comprising a suture connected to the needle, the needle comprising an attachment point between the first end and the second end; and wherein the suture is connected to the needle on at least one of the first end, the second end, and the attachment point.

17. A suturing system, comprising:
    a handle;
    a drive mechanism and a pivot drive mechanism mounted to the handle;
    a support body having a proximate end and a distal end, the proximate end connected to the pivot drive mechanism;
    a head mounted on the distal end of the support body, whereby the head rotates with the support body when the pivot drive mechanism is actuated;

at least one drive gear with a plurality of radially mounted outward protrusions mounted to the head;

at least one driveshaft connecting the drive mechanism and the at least one gear; and a needle with a first end, a second end, and a plurality of indentations therebetween, wherein the plurality of indentations engage with the plurality of outward protrusions of the drive gear to rotate the needle in a circular manner;

wherein a rotational plane of the needle is perpendicular to the support body.

18. The suturing system of claim 17, wherein at least one of the drive mechanism and the pivot drive mechanism is at least one of a stepper motor, a servo motor, a brushless motor, and a microgear DC motor with an encoder.

19. The suturing system of claim 17, wherein the first end comprises a pointed end to penetrate biological material.

20. The suturing system of claim 17, wherein the second end comprises a pointed end to penetrate biological material.

21. The suturing system of claim 17, further comprising a suture connected to the needle.

22. The suturing system of claim 21, wherein the needle further comprises an attachment point between the first end and the second end, and wherein the suture is connected to the needle on at least one of the first end, the second end, and the attachment point.

23. The suturing system of claim 17, wherein the needle comprises an arcuate shape with a contacting surface, and wherein the plurality of indentations are a repetitive machine pattern on the contacting surface.

* * * * *